US012673026B2

(12) United States Patent
Balcombe

(10) Patent No.: US 12,673,026 B2
(45) Date of Patent: *Jul. 7, 2026

(54) LIPOSOMAL COMPOSITIONS AND METHODS OF USE THEREOF FOR IMPROVED STABILITY, BIOAVAILABILITY AND SUSTAINED RELEASE

(71) Applicant: SpecNova LLC, Boca Raton, FL (US)

(72) Inventor: Sebastian Balcombe, Evergreen, CO (US)

(73) Assignee: SpecNova LLC, Tysons Center, VA (US)

( * ) Notice: Subject to any disclaimer, the term of this patent is extended or adjusted under 35 U.S.C. 154(b) by 177 days.

This patent is subject to a terminal disclaimer.

(21) Appl. No.: 18/736,168

(22) Filed: Jun. 6, 2024

(65) Prior Publication Data

US 2024/0408012 A1    Dec. 12, 2024

Related U.S. Application Data

(60) Provisional application No. 63/471,393, filed on Jun. 6, 2023.

(51) Int. Cl.
*A61K 9/1271*    (2025.01)
*A61K 45/06*    (2006.01)

(52) U.S. Cl.
CPC ............ *A61K 9/1271* (2013.01); *A61K 45/06* (2013.01)

(58) Field of Classification Search
None
See application file for complete search history.

(56) References Cited

U.S. PATENT DOCUMENTS

2008/0241917 A1 * 10/2008 Akita ................... A61K 9/1272
                                                                        435/320.1
2011/0229529 A1 * 9/2011 Irvine ................... A61K 39/39
                                                                        435/375
2015/0150801 A1 * 6/2015 Park ....................... A61K 31/44
                                                                        546/291

* cited by examiner

*Primary Examiner* — Brian J Davis
(74) *Attorney, Agent, or Firm* — Dentons Davis Brown; Matthew Coryell

(57) ABSTRACT

The embodiments disclosed herein relate to a liposomal composition for sustained release of an active ingredient. In various implementations, the liposomal composition may have a first liposomal core of Phosphatidylcholine (PC), phosphatidylethanolamine (PE), or phosphatidylserine (PS) and the active ingredient dispersed within the first liposomal core. A second core may surround the first liposomal core, with the second core optionally containing one or more polypeptide and a polysaccharide.

19 Claims, 21 Drawing Sheets

0th Day

240th Day

0<sup>th</sup> Day

240<sup>th</sup> Day

Disslolution of Encapsulated Berberine Chloride Products

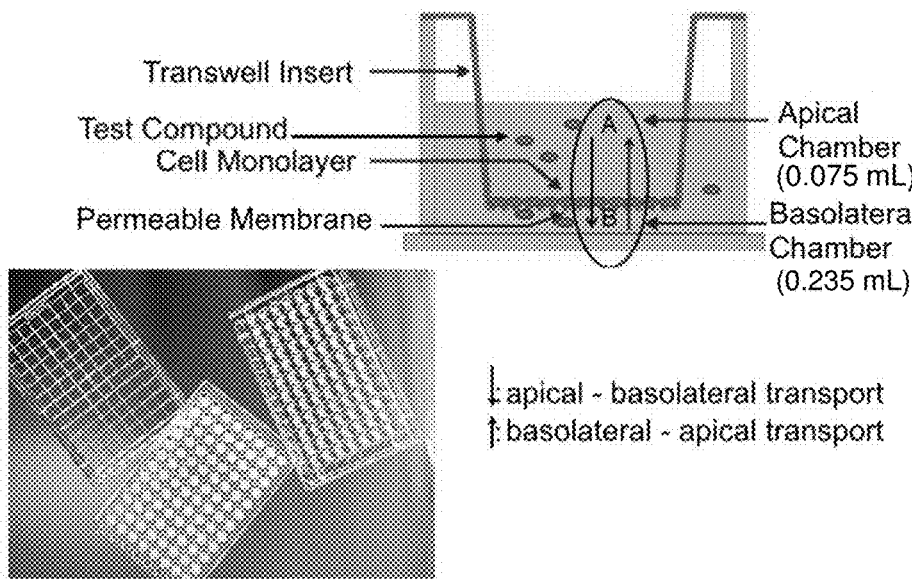

Caco-2 Tool Transwell Plate

↓ apical ~ basolateral transport
↑ basolateral ~ apical transport

Compounds permeate
through membrane Barrier

Incubate for 2 hr
Samples collected at 1h & 2h

LC-MS/MS Analysis

Compound Concentration
in Acceptor Well: $C_A$ (t)

Compound Concentration
in Donor Well: $C_D$ (t)

Permeability
Calculated from $C_A$
(t) & $C_D$ (t)

$$P_{app} = \left( \frac{V_A}{Area \times time} \right) \times \left( \frac{[drug]_{acceptor}}{[drug]_{initial,donor}} \right)$$

$P_{app} > 5*10^{-6}$ cm/Sec → High Permeability
$P_{app} < 5*10^{-6}$ cm/Sec → Low Permeability Where,
$V_D$ = donor volume (0.075 mL)
$V_A$ = acceptor volume (0.235 mL)
Area = membrane area (0.143 cm$^2$)
time = incubation time (in seconds)

FIG. 9

Compound name: Quercetin
Correlation coefficient: r = 0.998938, r^2 = 0.997678
Calibration curve: 0.0361354 * x + 0.0306697
Response type: Internal Std ( Ref 2 ), Area * ( IS Conc. / IS Area )
Curve type: Linear, Origin: Exclude, Weighting: 1/x, Axis trans: None Compound name: CoQ10 (880-197)
Correlation coefficient: r = 0.977193, r^2 = 0.954907
Calibration curve: 0.0881915 * x + 0.476936
Response type: Internal Std ( Ref 2 ), Area * ( IS Conc. / IS Area )
Curve type: Linear, Origin: Exclude, Weighting: 1/x, Axis trans: None Compound name: L-Carnosine
Correlation coefficient: r = 0.999815, r^2 = 0.999630
Calibration curve: 0.0643616 * x + -0.00138074
Response type: Internal Std ( Ref 4 ), Area * ( IS Conc. / IS Area )
Curve type: Linear, Origin: Exclude, Weighting: 1/x, Axis trans: None

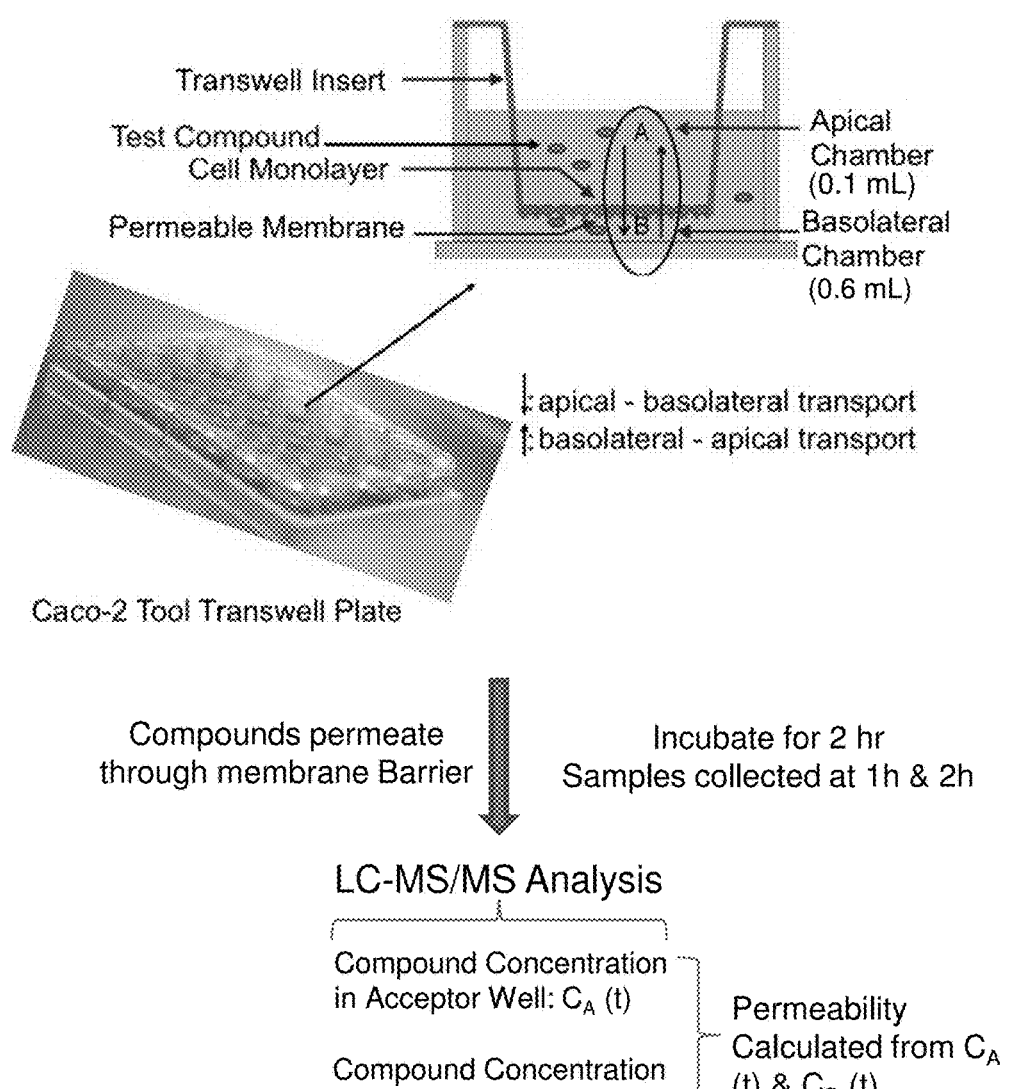

Transwell Insert

Test Compound

Cell Monolayer

Permeable Membrane

Apical Chamber (0.1 mL)

Basolateral Chamber (0.6 mL)

↓ apical - basolateral transport
↑ basolateral - apical transport

Caco-2 Tool Transwell Plate

Compounds permeate through membrane Barrier

Incubate for 2 hr
Samples collected at 1h & 2h

LC-MS/MS Analysis

Compound Concentration in Acceptor Well: $C_A$ (t)

Compound Concentration in Donor Well: $C_D$ (t)

Permeability Calculated from $C_A$ (t) & $C_D$ (t)

$$P_{app} \approx \left( \frac{V_A}{Area \times time} \right) \times \left( \frac{[drug]_{acceptor}}{[drug]_{initial,donor}} \right)$$

$P_{app} > 5*10^{-6}$ cm/Sec → High Permeability
$P_{app} < 5*10^{-6}$ cm/Sec → Low Permeability Where,
$V_D$ = donor volume (0.1 mL)
$V_A$ = acceptor volume (0.6 mL)
Area = membrane area (0.33 cm$^2$)
time = incubation time (in seconds)

FIG. 14

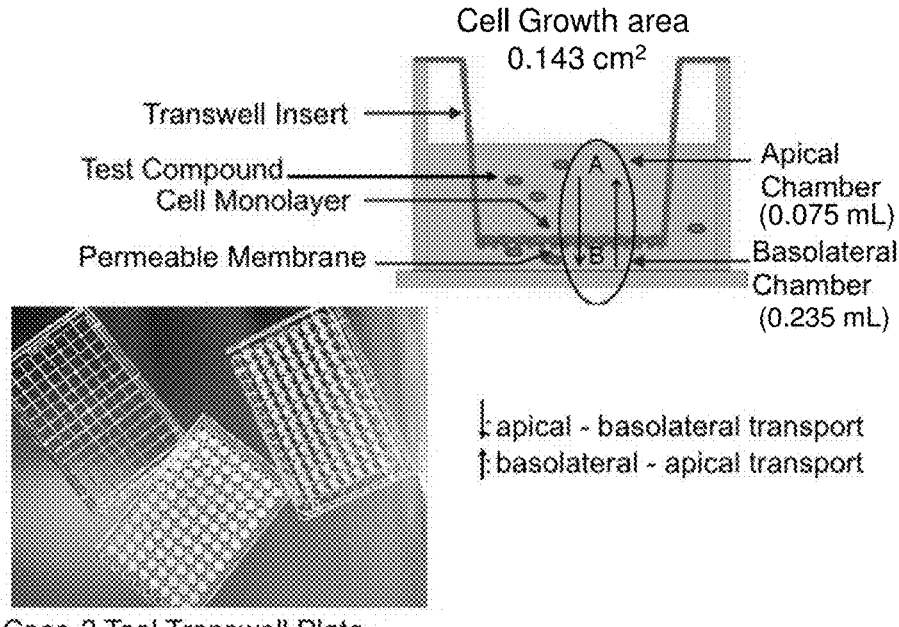

Cell Growth area
0.143 cm²

Transswell Insert

Test Compound
Cell Monolayer

Permeable Membrane

Apical Chamber (0.075 mL)

Basolateral Chamber (0.235 mL)

↓ apical - basolateral transport
↑ basolateral - apical transport

Caco-2 Tool Transwell Plate

Compounds permeate through membrane Barrier

Incubate for 2 hr
Samples collected at 1h & 2h

LC-MS/MS Analysis

Compound Concentration in Acceptor Well: $C_A$ (t)

Compound Concentration in Donor Well: $C_D$ (t)

Permeability Calculated from $C_A$ (t) & $C_D$ (t)

$$P_{app} = \left( \frac{V_A}{Area \times time} \right) \times \left( \frac{[drug]_{acceptor}}{[drug]_{initial,donor}} \right)$$

$P_{app} > 5*10^{-6}$ cm/Sec → High Permeability
$P_{app} < 5*10^{-6}$ cm/Sec → Low Permeability Where,
$V_D$ = donor volume (0.075 mL)
$V_A$ = acceptor volume (0.235 mL)
Area = membrane area (0.143 cm²)
time = incubation time (in seconds)

FIG. 17

Compound name: Quercetin
Correlation coefficient: r = 0.998938, r^2 = 0.997878
Calibration curve: 0.0361354 * x + 0.0306697
Response type: Internal Std ( Ref 2 ), Area * ( IS Conc. / IS Area )
Curve type: Linear, Origin: Exclude, Weighting: 1/x, Axis trans: None Compound name: Ascorbic Acid
Correlation coefficient: r = 0.996351, r^2 = 0.992716
Calibration curve: 0.00974285 * x + -0.190843
Response type: Internal Std ( Ref 2 ), Area * ( IS Conc. / IS Area )
Curve type: Linear, Origin: Exclude, Weighting: 1/x, Axis trans: None

LIPOSOMAL COMPOSITIONS AND METHODS OF USE THEREOF FOR IMPROVED STABILITY, BIOAVAILABILITY AND SUSTAINED RELEASE

CROSS-REFERENCE TO RELATED APPLICATION(S)

This application claims priority to U.S. Provisional Application No. 63/471,393 filed Jun. 6, 2023, and entitled "LIPOSOMAL COMPOSITIONS AND METHODS OF USE THEREOF FOR IMPROVED STABILITY, BIO-AVAILABILITY & SUSTAINED RELEASE", which is hereby incorporated by reference in its entirety under 35 U.S.C. § 119(c).

BACKGROUND

The low bioavailability of numerous dietary supplements poses a challenge to achieving their full potential efficacy. To overcome this issue, one approach that has been attempted is the use of delivery vehicles such as liposomes. These tiny globular concentric bilayer structures possess an aqueous core and are composed of relatively biodegradable, non-toxic, biocompatible, and low immunogenic phospholipids. These phospholipids are comprised of hydrophilic (polar) head and hydrophobic (non-polar) fatty acid tail. Despite the potential of liposomes as a delivery vehicle, they suffer from several drawbacks that limit their use, including limited loading capacity, liposomal leakage, and general instability. Therefore, there is a need in the art for improved liposomal compositions that address these and other shortcomings.

BRIEF SUMMARY

Disclosed herein is a liposomal composition for sustained release of an active having a first liposomal core comprising Phosphatidylcholine (PC), phosphatidylethanolamine (PE), phosphatidylserine (PS) and the active dispersed within the first liposomal core; and a second core surrounding the first liposomal core, the second core comprising one or more polypeptide and a polysaccharide. In certain embodiments, the amount of PC in the first liposomal core is at least about 50%. In certain embodiments, the amount of PE in the first liposomal core is from about 5-8%. In further embodiments, the amount of PS in the first liposomal core is from about 8-10%. In still further embodiments, the first liposomal core has a phase transition temperature of at least about 37° C.

According to certain embodiments, the second core polypeptide comprises pea protein hydrolysate and/or brown rice protein. In certain implementations, the second core polypeptide comprises at least about 10% dipeptides and tripeptides. In further embodiments, the second core polysaccharide comprises sodium hyaluronate, gum Arabic, sodium alginate and/or trehalose.

According to certain embodiments, the second core polysaccharide has a positive charge. In certain alternative embodiments, the second core polysaccharide has a negative charge.

According to certain embodiments, the liposomal composition further comprises a coating of ethyl cellulose. In exemplary implementations, the liposomal composition exhibits an increased in sustained release of the active relative to a comparable liposomal composition without a coating of ethyl cellulose.

According to certain embodiments, the liposomal composition has a diameter of about 200 nm or less. In certain further embodiments, the liposomal composition has a diameter of from about 140-185 nm. In still further embodiments, the liposomal composition has a diameter of about 145 nm.

According to certain embodiments, the liposomal composition has a zeta potential of from about −30.1 meV to about −61.8 meV.

According to certain embodiments, the liposomal composition is resistant to degradation in the stomach. In yet further embodiments, the liposomal composition preferentially releases the active in the small intestine.

In certain embodiments, the composition has an entrapment efficacy of at least about 80%. In certain embodiments, the liposomal composition remains stable for at least about 240 days.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

FIG. 9 is a diagram of the caco-2 stability method used with encapsulated berberine chloride products.

FIG. 14 is a diagram of the caco-2 stability method used with encapsulated L-carnosine products.

FIG. 17 is a diagram of the caco-2 stability method used with encapsulated quercetin products.

DETAILED DESCRIPTION

Figure 1:
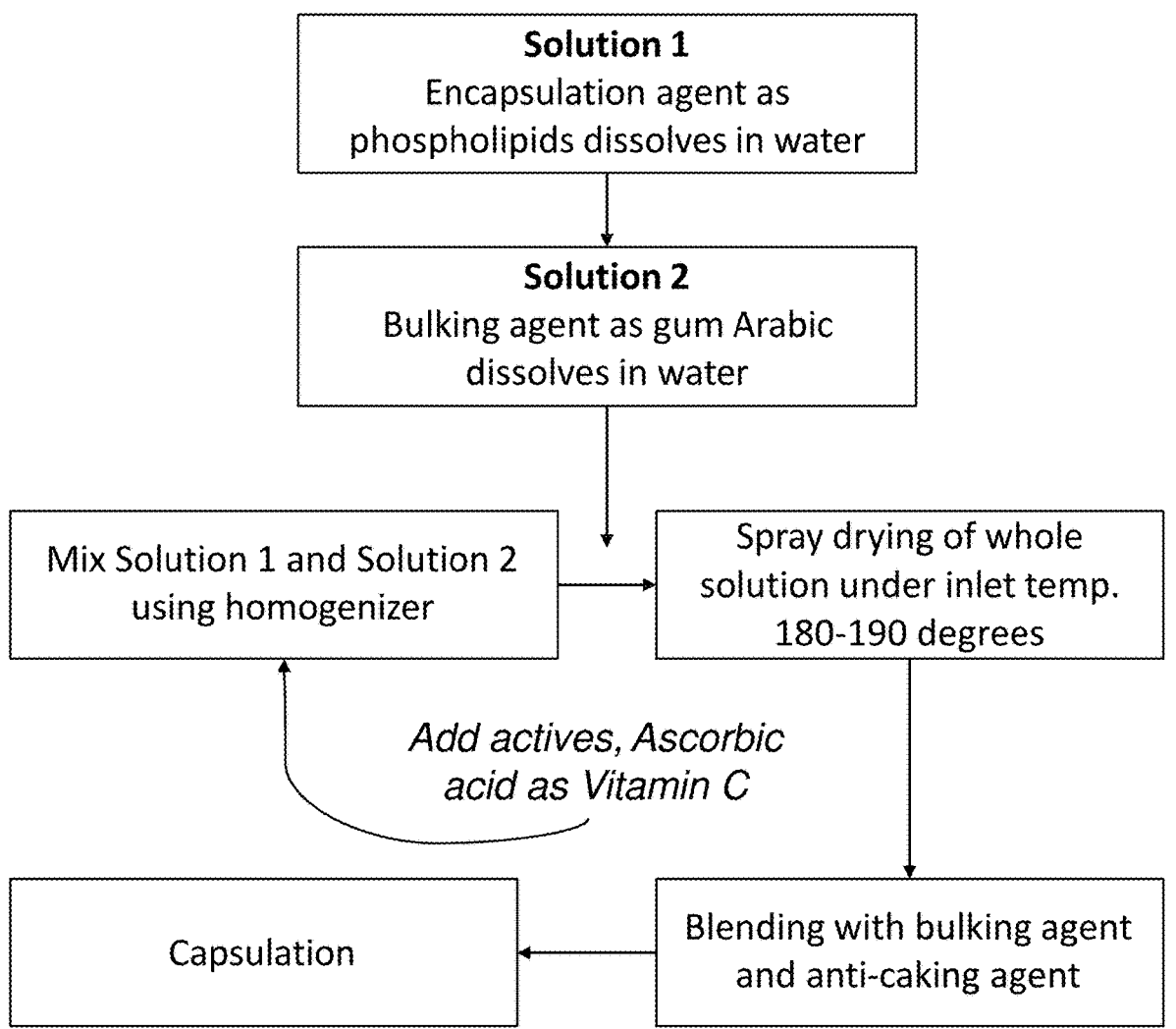
FIG. 1 is a flow chart for creating the vitamin C capsule, according to one implementation.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, WI), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of particles" would either completely lack particles, or so nearly completely lack particles that the effect would be the same as if it completely lacked particles. In other words, a composition that is "substantially free of an ingredient or element may still actually contain such item as long as there is no measurable effect thereof.

Admixing or admixed means the formation of a physical combination of two or more elements which may have a uniform or non-uniform composition throughout and includes, but is not limited to, solid mixtures, solutions and suspensions.

Aqueous and aqueous solution mean that water is present but does not require that water be the predominant component. For purposes of illustration and not in limitation, a solution of 90 volume percent of ethylene glycol and 10 volume percent water would be an aqueous solution. Aqueous solutions include liquid media containing dissolved or dispersed components such as, but not in limitation, colloidal suspensions and slurries.

The present disclosure relates to a liposomal composition for the sustained release of an active compound. More specifically, the invention provides a liposomal composition comprising a first liposomal core, with an active compound dispersed within the first liposomal core. The first liposomal core is surrounded by a second core comprising polypeptides and a polysaccharide. The liposomal composition exhibits enhanced stability and controlled release properties, making it suitable for various pharmaceutical and therapeutic applications.

The instantly disclosed composition can be used to deliver numerous actives, including, but not limited to: vitamins such as Vitamin C, Vitamin D, Vitamin E, and various B vitamins; minerals like calcium, magnesium, zinc, and iron; amino acids such as L-arginine, L-glutamine, and L-lysine; omega-3 fatty acids like EPA, DHA, and ALA; probiotics like *Lactobacillus acidophilus* and *Bifidobacterium lactis*; antioxidants such as CoQ10, resveratrol, and green tea extract; herbal extracts like *ginseng, Ginkgo biloba*, and *Echinacea*; enzymes such as bromelain and papain; fiber sources like *psyllium* husk and inulin; plant sterols and stanols like beta-sitosterol; prebiotics such as inulin and FOS; adaptogens like ashwagandha and *Rhodiola rosea*; collagen types I, II, and III; mushroom extracts like reishi and lion's mane; fruit and vegetable extracts like blueberry and broccoli.

First Liposomal Core

According to certain embodiments, the first liposomal core includes phosphatidylcholine (PC), phosphatidylethanolamine (PE), phosphatidylserine (PS), one or more phospholipids, and an active compound dispersed within the core. In certain embodiments, PC constitutes at least about 50% of the first liposomal core. PE is present in the range of about 5-8%, and PS is present in the range of about 8-10% in the first liposomal core. In certain implementations, the first liposomal core has a phase transition temperature of at least about 37° C., which ensures stability and controlled release of the active compound.

Second Core

According to certain embodiments, the second core surrounds the first liposomal core and consists of one or more polypeptides and a polysaccharide. In certain embodiments, polypeptides such as pea protein hydrolysate and/or brown rice protein are used in the second core. In exemplary implementations, the polypeptides contain at least about 10% dipeptides and tripeptides, which further enhance the sustained release properties of the liposomal composition.

According to certain embodiments, the polysaccharide in the second core can be sodium hyaluronate, gum Arabic, sodium alginate, and/or trehalose. The second core polysaccharide may have a positive or negative charge, allowing for customization of the liposomal composition.

Coating: In some embodiments, the liposomal composition may further comprise a coating of ethyl cellulose. The coating of ethyl cellulose provides additional protection to the liposomes and enhances the sustained release of the active compound. The presence of ethyl cellulose results in increased sustained release compared to a comparable liposomal composition without the coating.

Size and Zeta Potential

The liposomal composition has a diameter of about 200 nm or less, with a preferred diameter range of about 140-185 nm. In a specific embodiment, the liposomal composition has a diameter of about 145 nm.

Zeta potential is a scientific term used to describe the electrical potential that exists near the surface, specifically the slipping plane, of particles in a liquid medium. It is a key parameter in colloidal systems, including suspensions, emulsions, and nanoparticles. Zeta potential measurements provide valuable information about the stability and behavior of these colloidal systems. When a particle is suspended in a liquid, an electrical double layer forms around it. This double layer consists of two regions: the Stern layer, which is tightly bound to the particle surface and contains ions of the opposite charge to that of the particle, and the diffuse layer, which contains ions of the same charge as the particle and extends into the bulk liquid. The electrical potential difference between the particle surface and the bulk liquid is known as the zeta potential.

The liposomal composition also exhibits a zeta potential in the range of about −30.1 meV to about −61.8 meV, which influences the stability and targeting efficiency of the liposomes.

Stability and Entrapment Efficacy

According to certain embodiments, the liposomal composition remains stable for at least about 240 days, ensuring long-term shelf life and consistent performance. Additionally, the composition demonstrates an entrapment efficacy of at least about 80%, indicating efficient encapsulation of the active compound within the liposomes.

Gastrointestinal Compatibility: The liposomal composition is resistant to degradation in the stomach and preferentially releases the active compound in the small intestine. This characteristic ensures efficient delivery of the active compound to the desired site of action.

The liposomal composition described herein offers a versatile and effective approach to sustained release of active compounds. Its unique combination of liposomal and core components provides stability, controlled release, and protection for the encapsulated active compound, making it suitable for various nutraceutical and therapeutic applications.

According to certain embodiments, the instantly disclosed liposomal formulation and a novel preparation process provide highly unexpected effects, where intact liposomes with their contents inside are present in blood plasma. Previously, liposomes, when taken orally, have only been shown to help facility better solubility and permeability across the small intestines, where they separate from the active they are carrying, essentially acting as a shuttle through the cell membrane. Another aspect of the instantly disclosed composition is improved stability in the body, bioavailability and sustained release to a much greater extent than other liposomes.

EXPERIMENTAL

The following examples are put forth so as to provide those of ordinary skill in the art with a complete disclosure and description of how the compounds, compositions, articles, devices and/or methods claimed herein are made and evaluated and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Encapsulated liposomal vitamin C was created for the following examples following the process shown in FIG. 1.

Example 1: Cryo Transmission Electron Microscopic Images

Figures 2A, 2B:
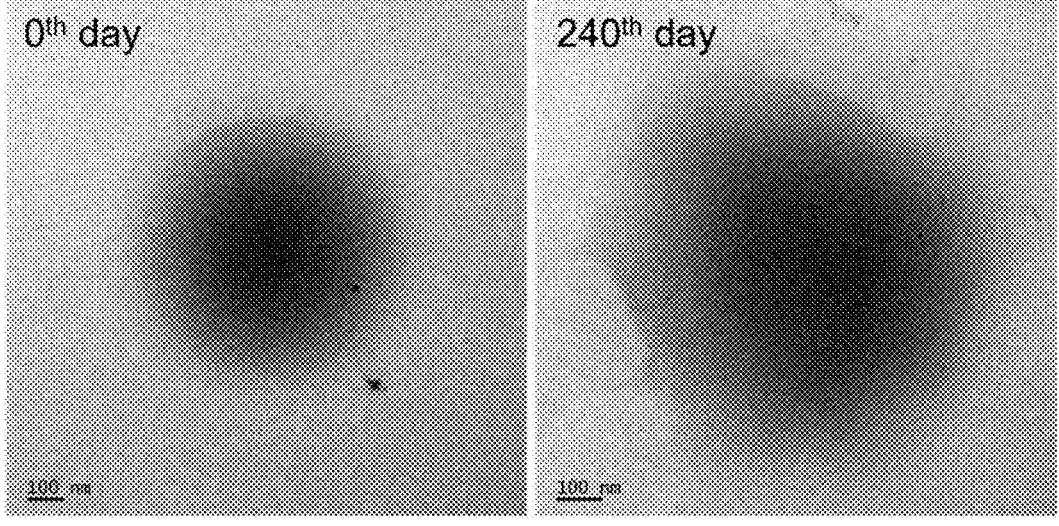
FIG. 2A shows a Cryo TEM image of a liposome at day 0.
FIG. 2B shows a Cryo TEM images of a liposome at day 240.
Figures 3A, 3B, 3C, 3D, 3E, 3F:
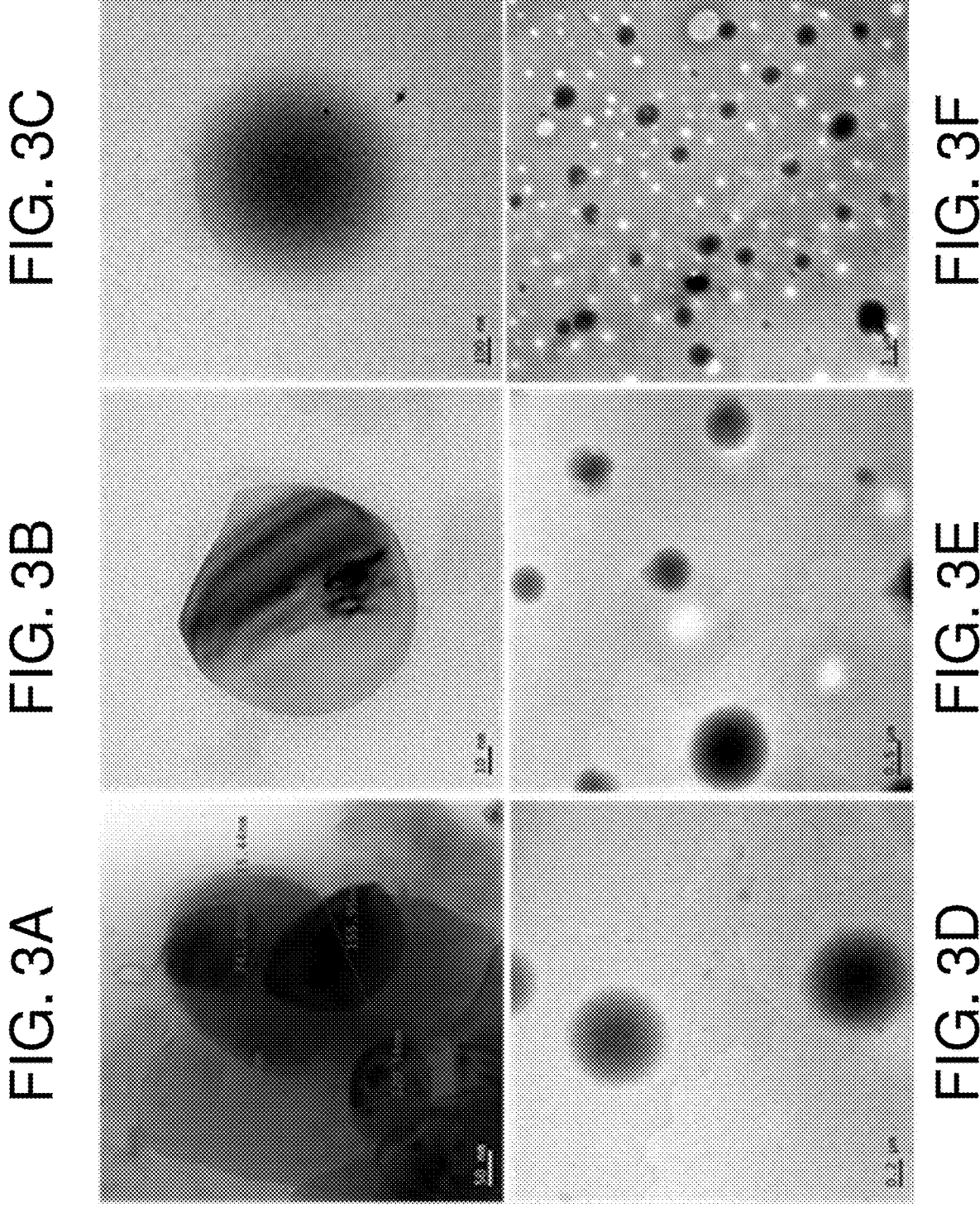
FIG. 3A shows a Cryo TEM image of a spray dried liposomal vitamin C.
FIG. 3B shows a Cryo TEM image of a spray dried liposomal vitamin C.
FIG. 3C shows a Cryo TEM image of a spray dried liposomal vitamin C.
FIG. 3D shows a Cryo TEM image of a spray dried liposomal vitamin C.
FIG. 3E shows a Cryo TEM image of a spray dried liposomal vitamin C.
FIG. 3F shows a Cryo TEM image of a spray dried liposomal vitamin C.

FIGS. 2A and 2B show Cryo TEM images of liposomes. There was minimal liposomal debris which, if present, might be indicative of vesicle rupture. Liposomes were spherical in shape and were well dispersed as indicated by the Cryo TEM images of FIGS. 2A and 2B. The core of liposomal structure was well defined as a dark portion, which is characteristic of a liposome.

The mean particle size of liposomes was calculated by image J software and found to be 145.00±4.58 nm. After conjugation with Vitamin C, the spherical morphology of liposomes, remained unaltered. The characterized spherical morphology of vitamin C encapsulated liposomes remain unaltered after 240 days, which indicates the stability of the product, as can be seen by comparing FIGS. 2A and 2B.

The results shown in this Example 1 were reproduceable in many batches of dry liposomal products. Cryo TEM images of spray dried liposomal vitamin C are shown in FIGS. 3A-F.

Example 2: Scanning Electron Microscopic Images

Figure 4:
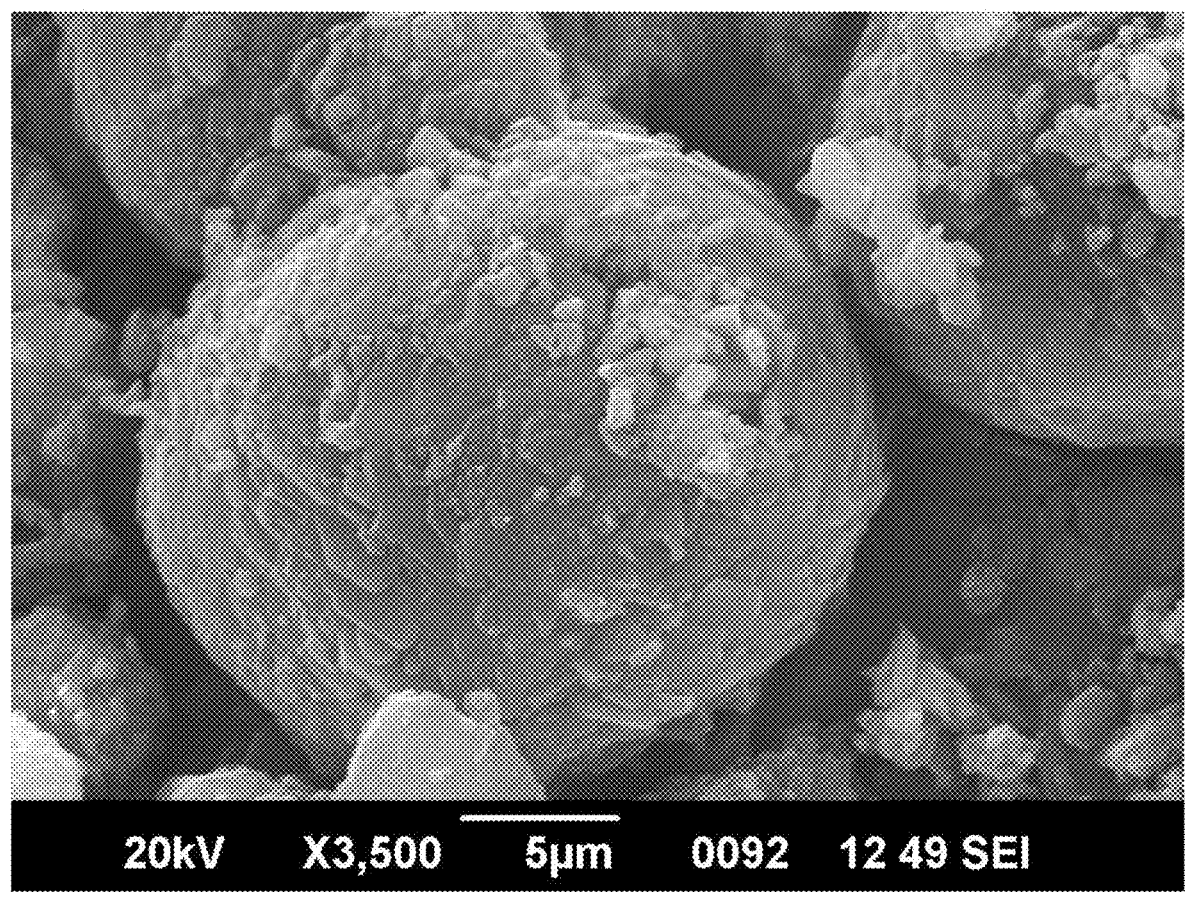
FIG. 4 is an SEM image of spray dried liposomal vitamin C.

SEM was used to understand the surface morphology of liposomes and implemented in the liposomal vitamin C capsules. It can be noted that the liposomes, which are developed as seen in FIG. 4, have a characteristic spherical structure with smooth surface.

Example 3: Dynamic Light Scattering Analysis (DLS)

Figure 5B:
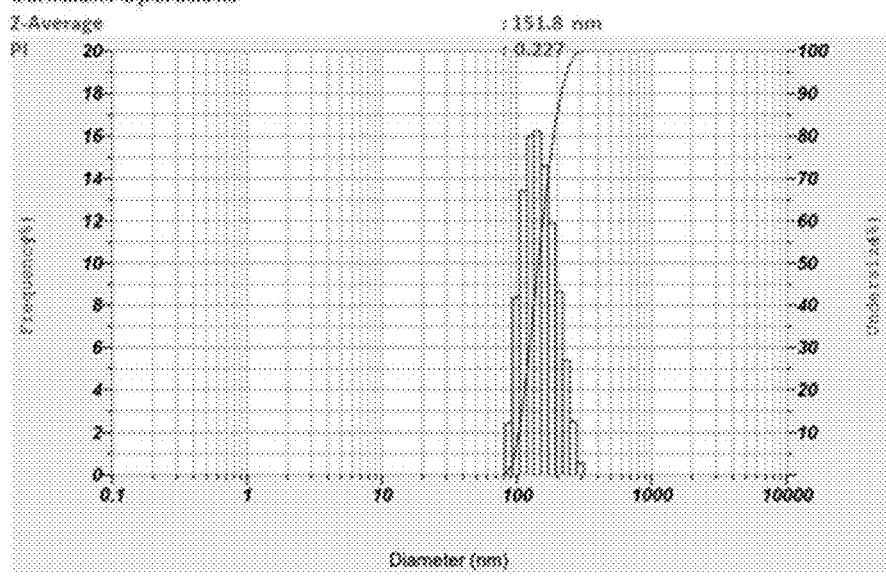
FIG. 5B is a DLS plot of spray dried liposomal vitamin C at day 240.
Figure 5A:
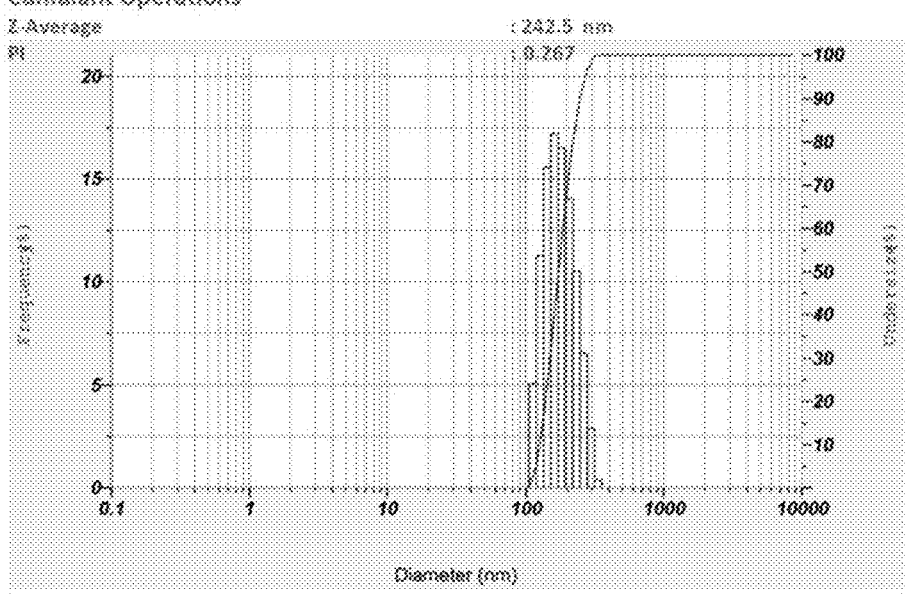
FIG. 5A is a DLS plot of spray dried liposomal vitamin C at day 0.

The nanostructures of the liposomes were confirmed via Cryo TEM, discussed above in Example 1, but Example 1 only analyzed a small number of a whole sample. As per the Einstein-Stokes relation, the nanomaterial was considered as a spherical particle because the principle of DLS is based on the scattered light intensity caused by Brownian motion of solvent without applying electric field. It is also noted that the DLS calculated hydrodynamic volume of suspension and therefore data derived from DLS analysis is different from the images. FIGS. 5A and 5B show the DLS images of Liposomal Vitamin C with new technology at days 0 and 240 respectively.

For the normal liposomal vitamin C sample, the largest number of particles (intensity) lies in the range of 150 nm-160 nm. It can be concluded from the DLS data that, the particle size of the product from day 0 to day 240 remains stable. This could be because of the formation of more compact structure (non-leaking) and repulsive forces bind the particles tightly to form a core shell like structure as evident from Cryo TEM images, discussed in Example 1.

The decrease in particle size may be desired because (1) as the size of the particle decreases, bioavailability (the chances to adsorb the same in the human body) increases; and (2) smaller particles result in more stable colloidal suspensions due to the increase in surface to volume ratio. This is an indication of stability of the product.

Example 4: Zeta Potential Measurements

Figure 6A:
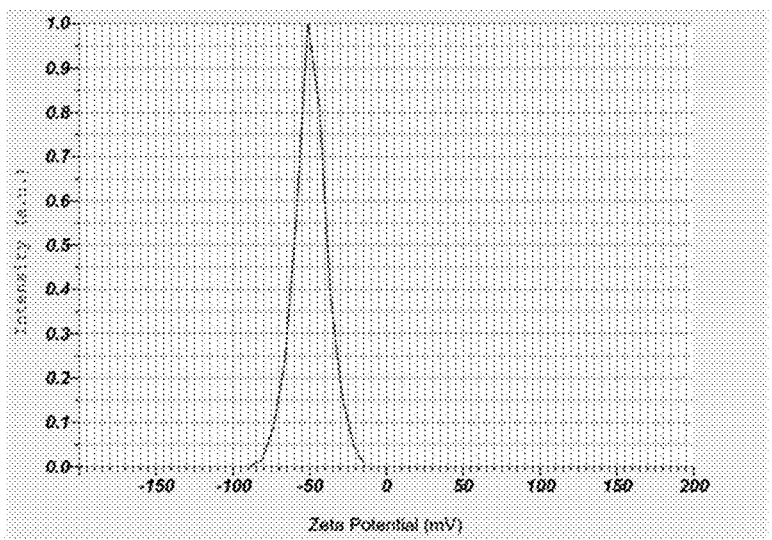
FIG. 6A is a Zeta Potential plot of liposomal vitamin C at day 0.
Figure 6B:
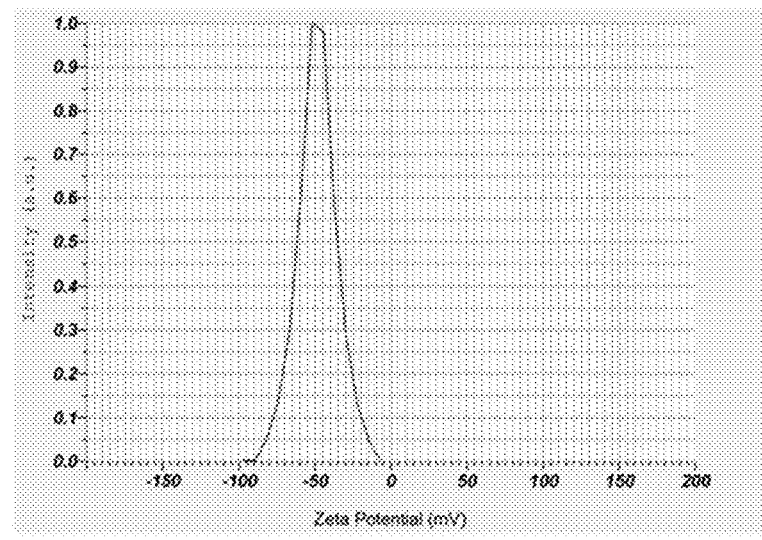
FIG. 6B is a Zeta Potential plot of liposomal vitamin C at day 240.

The zeta potential as measure of surface charge and is not only dependent on the pH but also on the ionic strength of the supporting electrolyte. In this case the zeta potential of liposomal Vitamin C is −30.8 mV at day 0 and remains unchanged after day 240 (−30.1 mV) which indicates higher colloidal stability, as shown in FIGS. 6A and 6B.

In this Example 4, with liposomal Vitamin C, the details of degradation during transit in the gastrointestinal tract were studied. Protection during digestion at low pH in the stomach, and at high pH in the presence of bile salt may be important for certain applications. By encapsulating vitamin C with liposome and covering that with the thin layer of Gum Arabic was shown to increases the stability of whole complex and thereby improve the slow release of active components, better biosorption and better bioavailability. The composition of the bilayer affects the pH stability and disruption in the presence of bile salts. The liposomes consist of surface charges which remain stable for a period of time which indicates there will be no leaking of active components, and an effective encapsulation and thereby potency retention.

Example 5: Mode of Delivery

Figure 7:
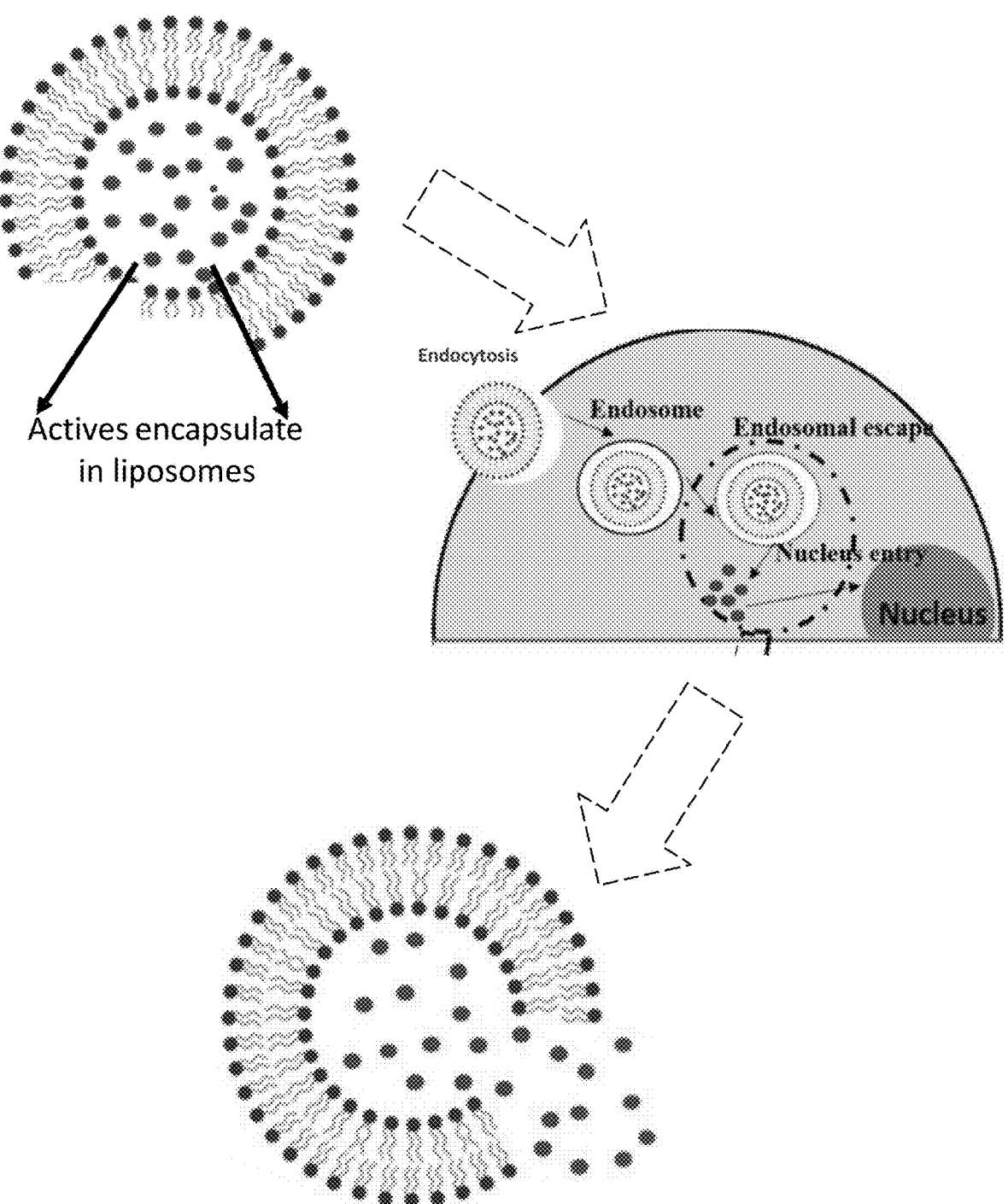
FIG. 7 is a schematic drawing showing the mode of delivery of active ingredient, mechanism of action.

A mode of delivery of the active ingredients from the encapsulated liposome is shown in FIG. 7.

Example 6: Liposomal Delivery Enhances Absorption of Vitamin C into Plasma and Leukocytes: A Double-Blind, Placebo-Controlled, Randomized Trial L-Ascorbic acid (vitamin C) is an essential water-soluble vitamin that plays an important role in various physiological functions, including immune health. The stability of vitamin C in the gastrointestinal tract and its bioavailability is limited. This study aimed to investigate if a liposomal form of vitamin C can increase absorption compared to standard vitamin C.

In a randomized, double-blind, placebo-controlled, cross-over fashion, 19 males and 8 females (n=27; 36.0±5.1 years, 165.0±6.9 cm, 70.6±7.1 kg) ingested a single-dose of placebo (PLA), 500 mg vitamin C (VIT C), and 500 mg liposomal vitamin C (LV-VIT C, Lipo Vantage®, Specnova, LLC, Tyson Corner, VA, USA). Venous blood samples were collected 0, 0.5-, 1-, 1.5-, 2-, 3-, 4-, 6-, 8-, 12-, and 24-hours after ingestion and were analyzed for plasma and leukocyte vitamin C concentration.

VIT C and LV-VIT C demonstrated significantly greater Cmax and AUC0-24 in plasma and in leukocytes compared to placebo (p<0.001). Additionally, LV-VIT C had significantly higher Cmax (plasma +27%, leukocytes +20%, p<0.001) and AUC0-24 (plasma +21%, leukocytes +8%, p<0.001) values as compared to VIT C.

In conclusion, liposomal formulation of vitamin C increases absorption into plasma and leukocytes.

Examples Using Various Target Compounds

In Examples 7-11, the disclosed technologies are employed with a variety of target products. Those products are berberine chloride for Example 7, CoQ10 for Example 8, L-carnosine for Example 9, quercetin for Example 10, and ascorbic acid for Example 11. These various compounds are tested within the disclosed liposomal compositions and compared to various standards, including the stand-alone compounds.

Example 7: Berberine Chloride Formulation Dissolution and Permeability Across Human Caco-2 Cells Monolayer Dissolution Procedure In this example, a known mass of the product was added to capsules at approximately 200 mg (n=2). 900 mL of potassium phosphate buffer at pH=7.4 was used in each well of the dissolution apparatus. Paddles (Type 2) were used 120 RPM and 37° C. Samples were drawn at 0, 5, 15, 30, 45, 60, 90, 120 minutes and immediately filtered. Samples were then diluted using 50:50 methanol:water and assayed with standards on the LC-MS/MS instrument.

From a primary stock (PS) at 10 μg/mL made from a Sigma Aldrich standard, a working stock (WS) at 2000 ng/mL was made. A standard curve from 10 to 1000 ng/mL was made from the WS using 50:50 methanol:water as diluent. Quality control standards were made at concentrations of 10, 30, 300, & 600 ng/mL. Verapamil as internal standard at 10 ng/ml was added to all samples, CS, and QC standards. The total analytical volume was 200 μL for all standards and samples and were analyzed by UPLC-MS/MS on the same day as preparation. Table 1 shows the amounts and concentrations used in this example.

Dissolution Results

Figure 8:
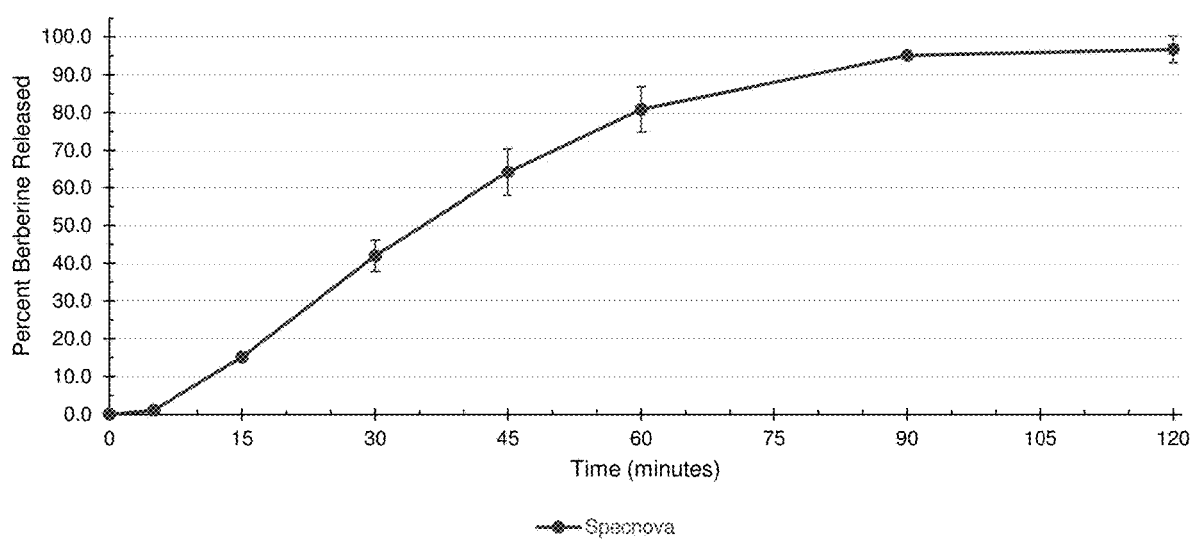
FIG. 8 is a graph of the dissolution of encapsulated berberine chloride products.

The target product, berberine chloride, had excellent dissolution, reaching saturation at approximately 90 minutes and 96 percent released (Based on 40% w/w compound in formulation). FIG. 8 and Table 2 summarize the results.

TABLE 2

| Example 7 Dissolution Test Results | |
| --- | --- |
| Time (minutes) | Target Product Percent Released ± SD |
| 0 | 0.0 ± 0.0 |
| 5 | 1.1 ± 0.0 |
| 15 | 15.1 ± 0.1 |
| 30 | 42.0 ± 4.1 |
| 45 | 64.2 ± 6.2 |
| 60 | 80.9 ± 6.0 |
| 90 | 95.1 ± 0.2 |
| 120 | 96.7 ± 3.5 |

Caco-2 Permeability Procedure

The study was performed using Caco-2 cells at a passage number of 38 seeded on a 24-well transwell plate. Berberine is insoluble in water which made it difficult to dissolve in water to make a stock. Instead, the formulation was added to the HBSS buffer at a concentration of 1 mg/mL, vortexed, and centrifuged for 15 min at 10,000 G-force. The supernatant was used for permeability assessment. For pure compound, the permeability study was performed at 10 μM final concentration. Compound solutions were added to the apical compartments of the transwell and blank buffer on the basolateral side. FIG. 9 provides a visual summary of this process.

Caco-2 Permeability Results

The target product had an almost 2× increase in permeability than the pure compound alone. Table 3 summarizes the results.

TABLE 3

| Example 7 Permeability Test Results | | |
| --- | --- | --- |
| Compound | Permeability ($P_{app}$) ($*10^{-6}$ cm/sec) A --> B | Permeability Class (High/ Low) |
| Sigma Aldrich Berberine Chloride | 2.17 ± 0.17 | Low |
| Target Berberine Chloride (liposomal) | 4.06 ± 0.22 | Low |
| Caffeine | 28.52 ± 1.25 | High |
| Atenolol | 3.71 ± 0.56 | Low |

Analytical Method

The parameters used in the analytical method of the example are as given below. Table 4 shows the HPLC

TABLE 1

| Example 7 Dissolution Test Concentrations | | | | | | | | | | | | |
| --- | --- | --- | --- | --- | --- | --- | --- | --- | --- | --- | --- | --- |
| CS | 1 | 2 | 3 | 4 | 5 | 6 | 7 | LLOQ | LQC | MQC | HQC | Unit |
| Concentration | 10 | 20 | 40 | 80 | 200 | 500 | 1000 | 10 | 30 | 300 | 600 | ng/ml |
| WS Conc. | 2000 | 2000 | 2000 | 2000 | 2000 | 2000 | 2000 | 2000 | 2000 | 2000 | 2000 | ng/mL |
| Vol of WS | 1 | 2 | 4 | 8 | 20 | 50 | 100 | 1 | 3 | 30 | 60 | μL |
| Vol of IS | 20 | 20 | 20 | 20 | 20 | 20 | 20 | 20 | 20 | 20 | 20 | μL |
| Vol of MeOH | 179 | 178 | 176 | 170 | 160 | 130 | 80 | 179 | 177 | 150 | 120 | μL |

Parameters. Table 5 shows the mass spectrometer parameters. Table 6 shows the UPLC Gradient.

Linearity range: 10-1000 ng/ml

Analysis type: UPLC-MS/MS (MRM scan)

Instrument: Waters Xevo TQ-S Micro & Waters Acquity I Class.

TABLE 4

Example 7 Permeability HPLC Parameters

| | |
|---|---|
| Mobile Phase A | 0.1% formic acid in water |
| Mobile Phase B | Acetonitrile |
| Flow Rate | 0.35 mL/min |
| Run Time | 3.0 minutes |
| Flow | Gradient |
| Column | Acquity UPLC BEH C18 1.7 μm, 2.1 mm × 50 mm |
| Column Temp | 40° C. |
| Sample Temp | 10° C. |
| Injection Volume | 2 μL |
| Weak Wash | 1:1:2 ACN:MeOH:water + 0.1% formic acid |
| Strong wash | 1:1:1:1 ACN:MeOH:IPA:water + 0.1% formic acid |
| Wash Volumes | Weak: 900 μL, Strong: 400 μL |

TABLE 5

Example 7 Permeability Mass Spectrometer Parameters

| | |
|---|---|
| Capillary Voltage | 3.00 kV |
| Desolvation Temp | 350° C. |
| Desolvation Gas Flow | 800 L/hr |
| Cone Gas Flow | 40 L/hr |
| Source Temp | 150° C. |

TABLE 6

Example 7 UPLC Gradient

| Time (min) | % A | Curve |
|---|---|---|
| Initial | 95 | Initial |
| 0.4 | 95 | 6 |
| 1.6 | 20 | 6 |
| 2.4 | 20 | 6 |
| 2.5 | 95 | 6 |
| 3.0 | 95 | 6 |

Calibration Curve and Representative Chromatogram

Figure 10A:
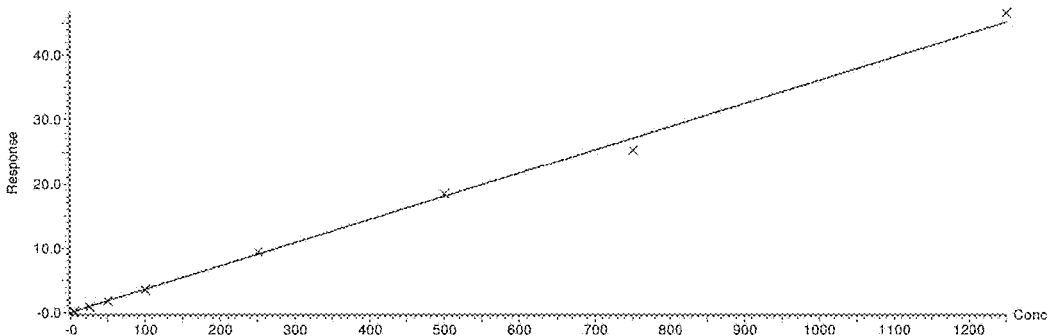
FIG. 10A is graph of a typical calibration curve for berberine chloride analysis.
Figure 10B:
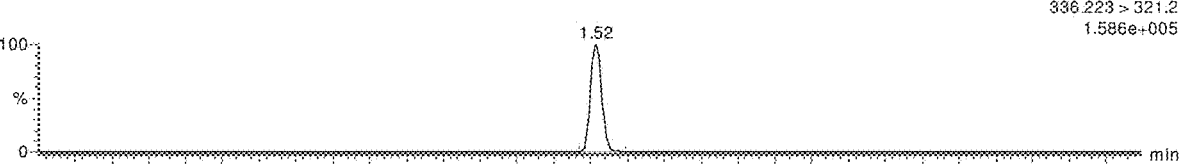
FIG. 10B is a chromatogram for Berberine.
Figure 10C:
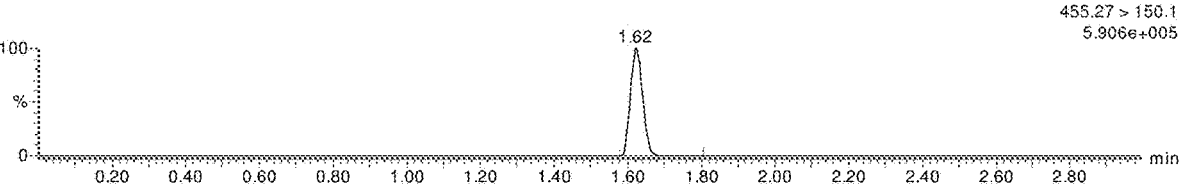
FIG. 10C is a chromatogram for verapamil, an internal standard.

FIG. 10A shows a typical calibration curve for Berberine Chloride Analysis. FIG. 10B shows a chromatogram for Berberine. FIG. 10C shows a chromatogram for verapamil, the internal standard.

Example 8: CoQ10 Formulation Dissolution and Permeability Across Human Caco-2 Cells Monolayer Dissolution Procedure In this example, a known mass of the product was added to capsules at approximately 200 mg (n=2). 900 mL of potassium phosphate buffer at pH=7.4 was used in each well of the dissolution apparatus. Paddles (Type 2) were used 120 RPM and 37° C. Samples were drawn at 0, 5, 15, 30, 45, 60, 90, 120 minutes and immediately filtered. Samples were then diluted using 50:50 methanol:water and assayed with standards on the LC-MS/MS instrument.

From a primary stock (PS) at 10 μg/mL made from a Sigma Aldrich standard, a working stock (WS) at 2000 ng/mL was made. A standard curve from 10 to 1000 ng/mL was made from the WS using 50:50 methanol:water as diluent. Quality control standards were made at concentrations of 10, 30, 300, & 600 ng/mL. Verapamil as internal standard at 10 ng/ml was added to all samples, CS, and QC standards. The total analytical volume was 200 μL for all standards and samples and were analyzed by UPLC-MS/MS on the same day as preparation. Table 7 shows the amounts and concentrations used in this example.

TABLE 7

Example 8 Dissolution Test Concentrations

| CS | 1 | 2 | 3 | 4 | 5 | 6 | 7 | LLOQ | LQC | MQC | HQC | Unit |
|---|---|---|---|---|---|---|---|---|---|---|---|---|
| Concentration | 10 | 20 | 40 | 80 | 200 | 500 | 1000 | 10 | 30 | 300 | 600 | ng/ml |
| WS Conc. | 2000 | 2000 | 2000 | 2000 | 2000 | 2000 | 2000 | 2000 | 2000 | 2000 | 2000 | ng/ml |
| Vol of WS | 1 | 2 | 4 | 8 | 20 | 50 | 100 | 1 | 3 | 30 | 60 | μL |
| Vol of IS | 20 | 20 | 20 | 20 | 20 | 20 | 20 | 20 | 20 | 20 | 20 | μL |
| Vol of MeOH | 179 | 178 | 176 | 170 | 160 | 130 | 80 | 179 | 177 | 150 | 120 | μL |

Dissolution Results

Unfortunately, the CoQ10 product did not release enough compound into solution to quantify. All samples were below limit of quantification (250 ng/ml; approximately 0.4% released based on 25% w/w compound in formulation).

It was noted that the capsule completely dissolved into the solution, however, there was a large amount of dark orange/brown sediment at the bottom of the dissolution wells after the experiment, very similar in color to the pure CoQ10 compound. It is probable that this sediment is the CoQ10 drug material that was not solubilized into the buffer during the experiment.

Caco-2 Permeability Procedure

The study was performed using Caco-2 cells at a passage number of 38 seeded on a 24-well transwell plate. CoQ10 is insoluble in water which made it difficult to dissolve in water to make a stock. Instead, the formulation was added to the HBSS buffer at a concentration of 1 mg/mL, vortexed, and centrifuged for 15 min at 10,000 G-force. The supernatant was used for permeability assessment. For pure compound, the permeability study was performed at 10 µM final concentration. Compound solutions were added to the apical compartments of the transwell and blank buffer on the basolateral side. FIG. 9 provides a visual summary of this process.

Caco-2 Permeability Results

The target product had significantly increased permeability compared to the pure compound, an over 8-fold increase. Table 8 summarizes the results.

TABLE 8

Example 8 Permeability Test Results

| Compound | Permeability ($P_{app}$) ($*10^{-6}$ cm/sec) A --> B | Permeability Class (High/Low) |
|---|---|---|
| CoQ10 Reference Standard | 0.2 ± 0.13 | Low |
| Target CoQ10 (liposomal) | 1.68 ± 0.69 | Low |
| Caffeine | 28.52 ± 1.25 | High |
| Atenolol | 3.71 ± 0.56 | Low |

Analytical Method

The parameters used in the analytical method of the example are as given below. Table 9 shows the HPLC Parameters. Table 10 shows the mass spectrometer parameters. Table 7 shows the transitions monitored.

Linearity range: 10-1000 ng/ml

Analysis type: UPLC-MS/MS (MRM scan)

Instrument: Waters Xevo TQ-S Micro & Waters Acquity I Class UPLC

TABLE 9

Example 8 Permeability HPLC Parameters

| | |
|---|---|
| Mobile Phase A | 0.1% formic acid in water |
| Mobile Phase B | Acetonitrile |
| Flow Rate | 0.35 mL/min |
| Run Time | 6.5 minutes |
| Flow | Isocratic |
| % A | 1% |
| % B | 99% |
| Column | Acquity UPLC BEH C18 1.7 µm, 2.1 mm × 50 mm |
| Column Temp | 40° C. |
| Sample Temp | 10° C. |
| Injection Volume | 2 L |
| Weak Wash | 1:1:2 ACN:MeOH:water + 0.1% formic acid |

TABLE 9-continued

Example 8 Permeability HPLC Parameters

| | |
|---|---|
| Strong wash | 1:1:1:1 ACN:MeOH:IPA:water + 0.1% formic acid |
| Wash Volumes | Weak: 900 µL, Strong: 400 µL |

TABLE 10

Example 8 Permeability Mass Spectrometer Parameters

| | |
|---|---|
| Capillary Voltage | 3.00 kV |
| Desolvation Temp | 350° C. |
| Desolvation Gas Flow | 800 L/hr |
| Cone Gas Flow | 40 L/hr |
| Source Temp | 150° C. |

TABLE 11

Example 8 Transitions Monitored

| | |
|---|---|
| CoQ10 [M + H]$^+$ | (Quantifier) m/z 880.7 > 197.0 |
| | Cone Voltage: 4 V, Collision Voltage: 16 V |
| CoQ10 [M + H]$^+$ | (Qualifier) m/z 880.7 > 109.0 |
| | Cone Voltage: 4 V, Collision Voltage: 30 V |
| Verapamil [M + H]$^+$ | (IS) m/z 455.3 > 150.1 |
| | Cone Voltage: 28 V, Collision Voltage: 42 V |

Calibration Curve and Representative Chromatogram

Figure 11A:
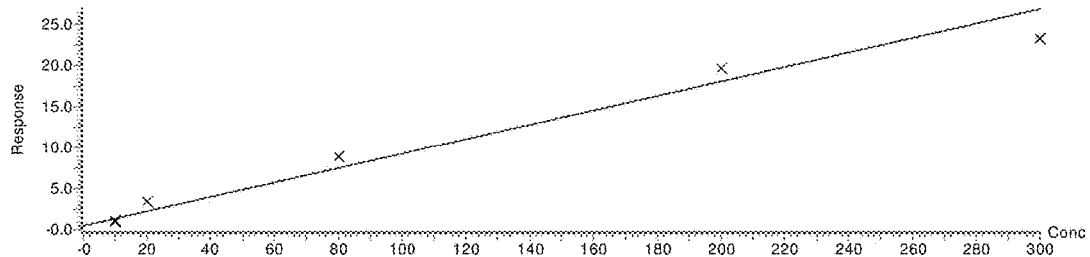
FIG. 11A is graph of a typical calibration curve for CoQ10 analysis.
Figure 11B:
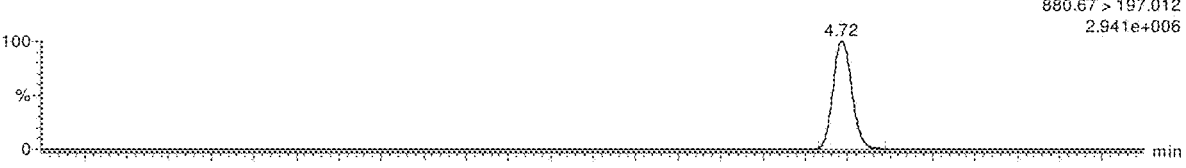
FIG. 11B is a chromatogram for CoQ10.
Figure 12A:
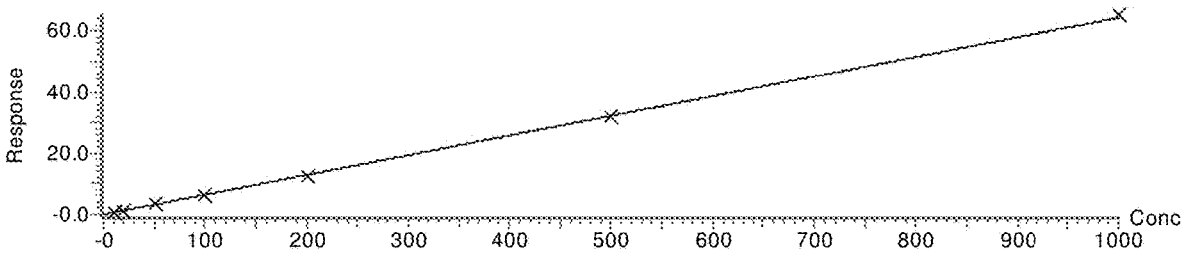
FIG. 12A is graph of a typical calibration curve for L-carnosine analysis.
Figure 12B:
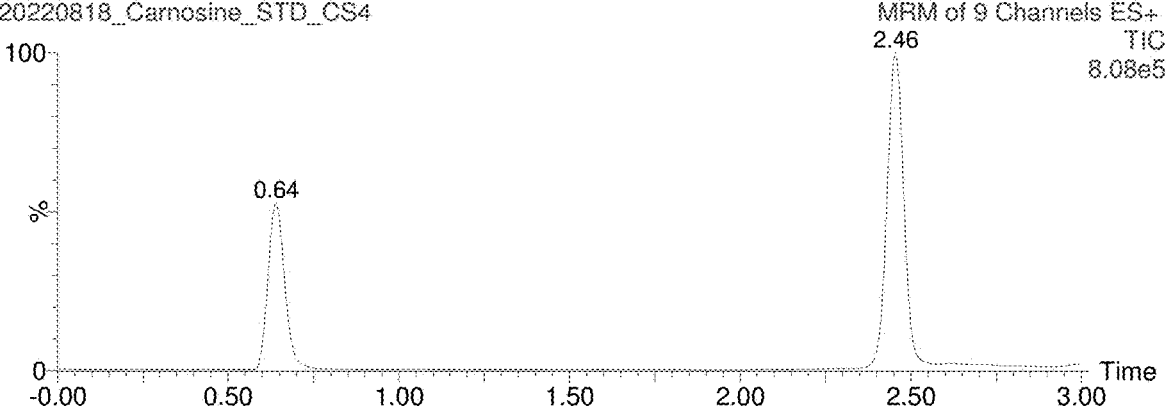
FIG. 12B is a chromatogram for L-carnosine.

FIG. 11A shows a typical calibration curve for CoQ10 Analysis. FIG. 11B shows a chromatogram for CoQ10.

Example 9: L-Carnosine Stability in Simulated Gastric and Intestinal Fluids and Permeability Across Human Colorectal Adenocarcinoma Cells (Caco-2)

Experimental Conditions

Three fluids were simulated: fasted (pH 1.2) and fed (pH 3.5) simulated gastric fluid (SGF) and simulated intestinal fluid (SIF) (pH 6.8). The experimental concentration was 10 µM and performed in an incubator/shaker at 37.0° C. and 125 RPM. A zero time point was taken after adding the appropriate stock to each fluid (N=2) and mixed by pipette. Time points were then taken at 5, 10, 15, 30, 60, 90, and 120 minutes. These were quenched with ACN and kept on ice. The samples were then added to 50% ACN in 2.5 nM ammonium acetate buffer (pH=3.6) with Verapamil for Internal Standard (IS) and filtered before analysis.

Analysis

Two concentrations of working stocks were made at 5000 ng/ml and 200 ng/ml. Calibration & QC standards were made as shown in Table 12. In Table 12, diluent is 50% ACN in 2.5 nM ammonium acetate buffer (pH=3.6). The total analytical volume was 200 µL for all standards and samples. Six sets of QCs were used along with the samples and seven calibration standards. All were analyzed by UPLC-MS/MS on the same day as preparation.

TABLE 12

Example 9 Dissolution Test Concentrations

| Standard | 1 | 2 | 3 | 4 | 5 | 6 | 7 | LLOQ | LQC | MQC | HQC | Unit |
|---|---|---|---|---|---|---|---|---|---|---|---|---|
| Concentration | 10 | 20 | 50 | 100 | 200 | 500 | 1000 | 10 | 20 | 500 | 1000 | ng/ml |
| WS Conc. | 200 | 200 | 200 | 200 | 5000 | 5000 | 5000 | 200 | 200 | 5000 | 5000 | ng/ml |
| Vol of WS | 10 | 20 | 50 | 100 | 8 | 20 | 40 | 10 | 20 | 20 | 40 | µL |
| Vol of IS | 100 | 100 | 100 | 100 | 100 | 100 | 100 | 100 | 100 | 100 | 100 | µL |
| Vol of Diluent | 90 | 80 | 50 | 0 | 92 | 80 | 60 | 90 | 80 | 80 | 60 | µL |

Analytical Method

The parameters used in the analytical method of the example are as given below. Table 13 shows the HPLC Parameters. Table 14 shows the mass spectrometer parameters. Table 15 shows the UPLC Gradient.

Sample volume: 200 μL

Linearity range: 10-1000 ng/ml

Analysis type: HPLC-MS/MS

TABLE 13

Example 9 Permeability HPLC Parameters

| | |
|---|---|
| Mobile Phase A | 2.5 mM ammonium acetate (pH 3.6) |
| Mobile Phase B | Acetonitrile |
| Flow Rate | 0.35 mL/min |
| Flow | Gradient |
| Column | Acquity UPLC HSS T3 1.7 μm, 2.1 mm × 100 mm |
| Injection Volume | 2 μL |

TABLE 14

Example 9 Permeability Mass Spectrometer Parameters

| | |
|---|---|
| L-Carnosine (Quantifier) | m/z 227.15 > 109.90 |
| L-Carnosine (Qualifier) | m/z 227.15 > 155.95 |
| Verapamil (Internal Standard) | m/z 455.27 > 150.10 |

TABLE 15

Example 9 UPLC Gradient

| Time (min) | % A | Curve |
|---|---|---|
| Initial | 94 | Initial |
| 0.75 | 94 | 6 |
| 1.80 | 25 | 6 |
| 2.50 | 25 | 6 |
| 3.00 | 94 | 1 |

Results

Figure 13:
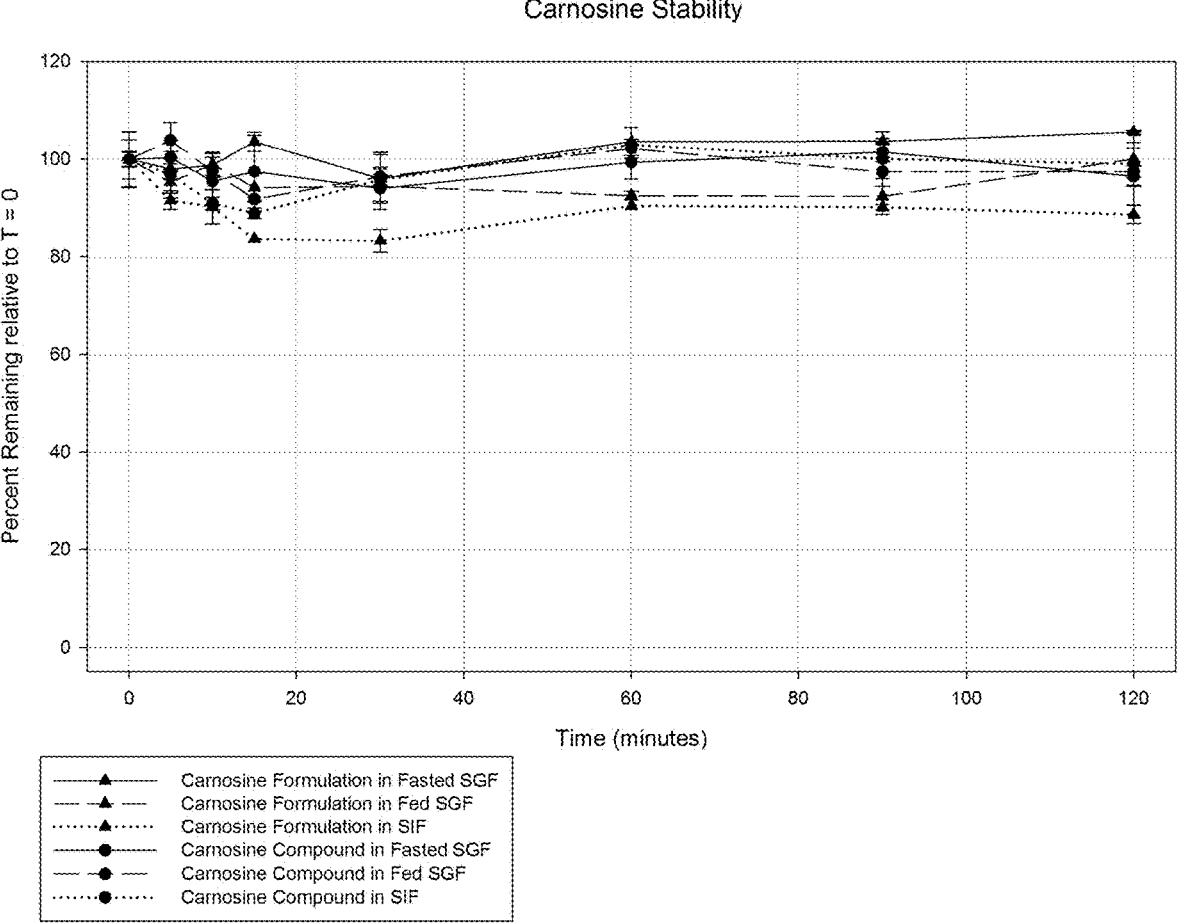
FIG. 13 is a graph of L-carnosine stability.

FIG. 13 and Tables 16 and 17 summarize the results of this example. Both L-carnosine and L-carnosine formulation (target) were found stable in SGF and SIF.

TABLE 16

Example 9 Results part 1

| | Carnosine Formulation | | | | | |
|---|---|---|---|---|---|---|
| | Fasted SGF | | Fed SGF | | SIF | |
| Time | % Remaining | SD | % Remaining | SD | % Remaining | SD |
| 0 | 100 | 5.7 | 100 | 1.6 | 100 | 5.6 |
| 5 | 98 | 5.9 | 95.4 | 2.2 | 91.7 | 1.9 |
| 10 | 98.8 | 2.4 | 99 | 2.2 | 90.3 | 3.5 |
| 15 | 103.6 | 2 | 94.2 | 2.9 | 83.7 | 0 |
| 30 | 96 | 5 | 94.5 | 3.5 | 83.3 | 2.4 |
| 60 | 103.7 | 2.9 | 92.6 | 0.9 | 90.5 | 0 |
| 90 | 103.7 | 0.6 | 92.5 | 3.6 | 90.2 | 0.5 |
| 120 | 105.6 | 0.4 | 100.1 | 5.6 | 88.7 | 1.8 |

Where N = 2 for each sample
SGF = Simulated Gastric Fluid
SD = Standard deviation
SIF = Simulated Intestinal Fluid

TABLE 17

Example 9 Results part 2

| | Carnosine | | | | | |
|---|---|---|---|---|---|---|
| | Fasted SGF | | Fed SGF | | SIF | |
| Time | % Remaining | SD | % Remaining | SD | % Remaining | SD |
| 0 | 100 | 1.4 | 100 | 4 | 100 | 0.3 |
| 5 | 100.3 | 1.3 | 103.9 | 3.7 | 96.9 | 1 |
| 10 | 95.5 | 4.9 | 97.6 | 3.8 | 91 | 1.3 |
| 15 | 97.5 | 7.5 | 91.9 | 0.4 | 89 | 1 |
| 30 | 94 | 4.3 | 96.5 | 5 | 95.8 | 1 |
| 60 | 99.4 | 3.4 | 102.2 | 1.9 | 103 | 0.2 |
| 90 | 101.5 | 2 | 97.4 | 2.9 | 100.1 | 5.6 |
| 120 | 96.5 | 5.8 | 97.4 | 1.2 | 99.1 | 4.4 |

Where N = 2 for each sample
SGF = Simulated Gastric Fluid
SD = Standard deviation
SIF = Simulated Intestinal Fluid

Permeability Across Human Colorectal Adenocarcinoma Cells (Caco-2)

A diagram of the setup used for this study is shown in FIG. 14. The study was performed using Caco-2 cells at a passage number of 26 seeded on a 24-well transwell plates. The permeability of carnosine was studied at a concentration of 20 μM. Compounds were solubilized in HBSS and added to apical compartment of transwells and blank buffer on basolateral side. Permeability of carnosine formulation (target) across the Caco-2 cell monolayer was similar to carnosine. Table 18 summarizes the results.

TABLE 18

Example 9 Permeability of Carnosine

| Compound | Permeability ($P_{app}$) ($*10^{-6}$ cm/sec) A-->B | Permeability Class (High/Low) |
|---|---|---|
| Carnosine | 3.05 ± 0.62 | Low |
| Target Carnosine (Liposomal) | 3.34 ± 0.3 | Low |
| Caffeine | 63.82 ± 13.29 | High |
| Atenolol | 1.91 ± 0.48 | Low |

Example 10: Quercetin Formulation Quantification, Dissolution, Stability in Gastrointestinal Fluids, and Permeability Across Human Caco-2 Cells Monolayer

Quantitation Procedure

In this example, A known mass of each product was diluted three test solutions, 100% water, 100% methanol, & 50:50 methanol:water at a concentration of 1 mg/mL. These were mixed and sonicated well before filtering and diluting with 50:50 methanol:water to a concentration of 2500 ng/mL. Verapamil was used as an internal standard.

From a primary stock (PS) at 10 μg/mL made from a USP reference standard, two working stocks (WS) at 5000 & 500 ng/mL were made. A standard curve from 10 to 2500 ng/ml was made from the WS using 50:50 methanol:water as diluent. Quality control standards were made at concentrations of 10, 50, 500, & 2000 ng/mL. Verapamil as internal standard at 10 ng/ml was added to all samples, CS, and QC standards. Table 19 shows the amounts and concentrations used in this example.

TABLE 19

| | | | | | | | | | | | | | |
|---|---|---|---|---|---|---|---|---|---|---|---|---|---|
| Example 10 Quantitation Test Concentrations | | | | | | | | | | | | | |
| CS | 1 | 2 | 3 | 4 | 5 | 6 | 7 | 8 | LLOQ | LQC | MQC | HQC | Unit |
| Concentration | 10 | 50 | 100 | 200 | 500 | 1000 | 1500 | 2500 | 10 | 50 | 500 | 2000 | ng/ml |
| WS Conc. | 500 | 500 | 500 | 500 | 5000 | 5000 | 5000 | 5000 | 500 | 500 | 500 | 500 | ng/ml |
| Vol of WS | 4 | 20 | 40 | 80 | 20 | 40 | 60 | 100 | 4 | 20 | 20 | 80 | μL |
| Vol of IS | 20 | 20 | 20 | 20 | 20 | 20 | 20 | 20 | 20 | 20 | 20 | 20 | μL |
| Vol of MeOH | 176 | 160 | 140 | 100 | 160 | 140 | 120 | 80 | 176 | 160 | 160 | 100 | μL |

The total analytical volume was 200 μL for all standards and samples and were analyzed by UPLC-MS/MS on the same day as preparation.

Quantitation Results

For the target product, 50:50 water:methanol showed the highest peak area, while the competitor product showed highest in 100% methanol. The target product sample had a 44.6% w/w ratio, while the competitor product sample had a 41.8% w/w ratio.

Dissolution Procedure

A known mass of each product was added to capsules at approximately 200 mg (n=2). 900 mL of Potassium phosphate buffer at pH=6.8 was used in each well of the dissolution apparatus. Paddles (Type 2) were used 75 RPM and 37° C. Samples were drawn at 0, 5, 15, 30, 45, 60, 90, 120 minutes and immediately filtered. Samples were then diluted using 50:50 methanol:water and assayed with standards on the LC-MS/MS instrument.

From a primary stock (PS) at 10 μg/mL made from a USP reference standard, two working stocks (WS) at 5000 & 500 ng/mL were made. A standard curve from 10 to 2500 ng/mL was made from the WS using 50:50 methanol:water as diluent. Quality control standards were made at concentrations of 10, 50, 500, & 2000 ng/mL. Verapamil as internal standard at 10 ng/mL was added to all samples, CS, and QC standards. Table 20 summarizes this information.

TABLE 21

| | | | | | | | | | | | | | |
|---|---|---|---|---|---|---|---|---|---|---|---|---|---|
| Example 10 Dissolution Test Concentrations | | | | | | | | | | | | | |
| CS | 1 | 2 | 3 | 4 | 5 | 6 | 7 | 8 | LLOQ | LQC | MQC | HQC | Unit |
| Concentration | 10 | 50 | 100 | 200 | 500 | 1000 | 1500 | 2500 | 10 | 50 | 500 | 2000 | ng/ml |
| WS Conc. | 500 | 500 | 500 | 500 | 5000 | 5000 | 5000 | 5000 | 500 | 500 | 500 | 500 | ng/mL |
| Vol of WS | 4 | 20 | 40 | 80 | 20 | 40 | 60 | 100 | 4 | 20 | 20 | 80 | μL |
| Vol of IS | 20 | 20 | 20 | 20 | 20 | 20 | 20 | 20 | 20 | 20 | 20 | 20 | μL |
| Vol of MeOH | 176 | 160 | 140 | 100 | 160 | 140 | 120 | 80 | 176 | 160 | 160 | 100 | μL |

The total analytical volume was 200 μL for all standards and samples and were analyzed by UPLC-MS/MS on the same day as preparation.

Dissolution Results

Figure 15:
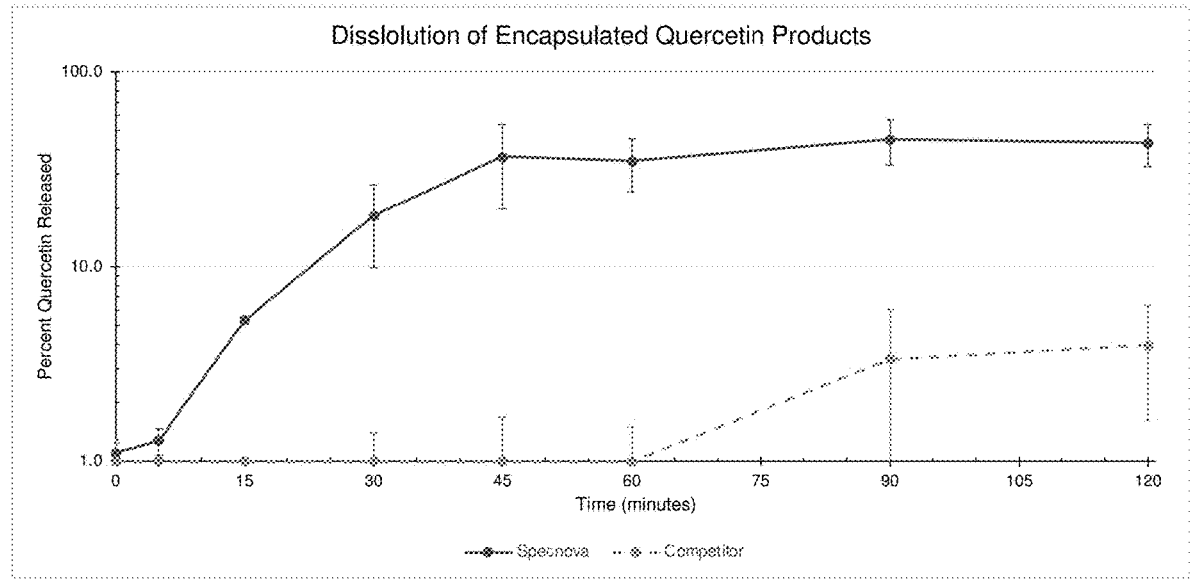
FIG. 15 is a graph of the dissolution of encapsulated quercetin products.

The target product reached saturation at approximately 90 minutes, while the competitor did reach saturation within the two-hour experiment. FIG. 15 and Table 22 summarize the results. The target product showed a better dissolution profile than competitor product.

TABLE 22

| | | |
|---|---|---|
| Example 10 Dissolution Test Results | | |
| Time (minutes) | Target Product Percent Released ± SD | Competitor Product Percent Released ± SD |
| 0 | 1.1 ± 0.1 | 0.7 ± 0.3 |
| 5 | 1.3 ± 0.2 | 0.4 ± 0.5 |
| 15 | 5.3 ± 0.2 | 0.2 ± 0.0 |
| 30 | 18.2 ± 8.3 | 0.5 ± 0.4 |
| 45 | 36.9 ± 17.1 | 0.7 ± 0.7 |
| 60 | 34.9 ± 10.8 | 0.8 ± 0.5 |
| 90 | 45.3 ± 12.0 | 3.3 ± 2.7 |
| 120 | 43.3 ± 10.6 | 4.0 ± 2.3 |

Stability Procedure

Three fluids were simulated: fasted (pH 1.29) and fed (pH 3.41) simulated gastric fluid (SGF) and simulated intestinal fluid (SIF) (pH 6.71). The experimental concentration was approximately 3 μg/mL for all products based on the % w/w calculated previously and performed in an incubator/shaker at 37.0° C. and 125 RPM. A zero time point was taken after adding the appropriate stock to each fluid (N=2) and mixed by pipette. Time points were then taken at 5, 10, 15, 30, 60, 90, and 120 minutes. These were quenched with ACN and kept on ice until analysis. The samples were then added to 50:50 methanol:water with verapamil as internal standard (IS) and filtered before analysis.

From a primary stock (PS) at 10 μg/mL made from a USP reference standard, two working stocks (WS) at 5000 & 500 ng/mL were made. A standard curve from 10 to 2500 ng/ml was made from the WS using 50:50 methanol:water as diluent. Quality control standards were made at concentrations of 10, 50, 500, & 2000 ng/mL. Verapamil as internal standard at 10 ng/ml was added to all samples, CS, and QC standards. Table 23 summarizes this information.

TABLE 23

| | | | | | | | | | | | | | |
|---|---|---|---|---|---|---|---|---|---|---|---|---|---|
| | | | | | Example 10 Stability Test Concentrations | | | | | | | | |
| CS | 1 | 2 | 3 | 4 | 5 | 6 | 7 | 8 | LLOQ | LQC | MQC | HQC | Unit |
| Concentration | 10 | 50 | 100 | 200 | 500 | 1000 | 1500 | 2500 | 10 | 50 | 500 | 2000 | ng/ml |
| WS Conc. | 500 | 500 | 500 | 500 | 5000 | 5000 | 5000 | 5000 | 500 | 500 | 500 | 500 | ng/ml |
| Vol of WS | 4 | 20 | 40 | 80 | 20 | 40 | 60 | 100 | 4 | 20 | 20 | 80 | μL |
| Vol of IS | 20 | 20 | 20 | 20 | 20 | 20 | 20 | 20 | 20 | 20 | 20 | 20 | μL |
| Vol of MeOH | 176 | 160 | 140 | 100 | 160 | 140 | 120 | 80 | 176 | 160 | 160 | 100 | μL |

The total analytical volume was 200 μL for all standards and samples and were analyzed by UPLC-MS/MS on the same day as preparation.

Stability Results

Figures 16A, 16B:
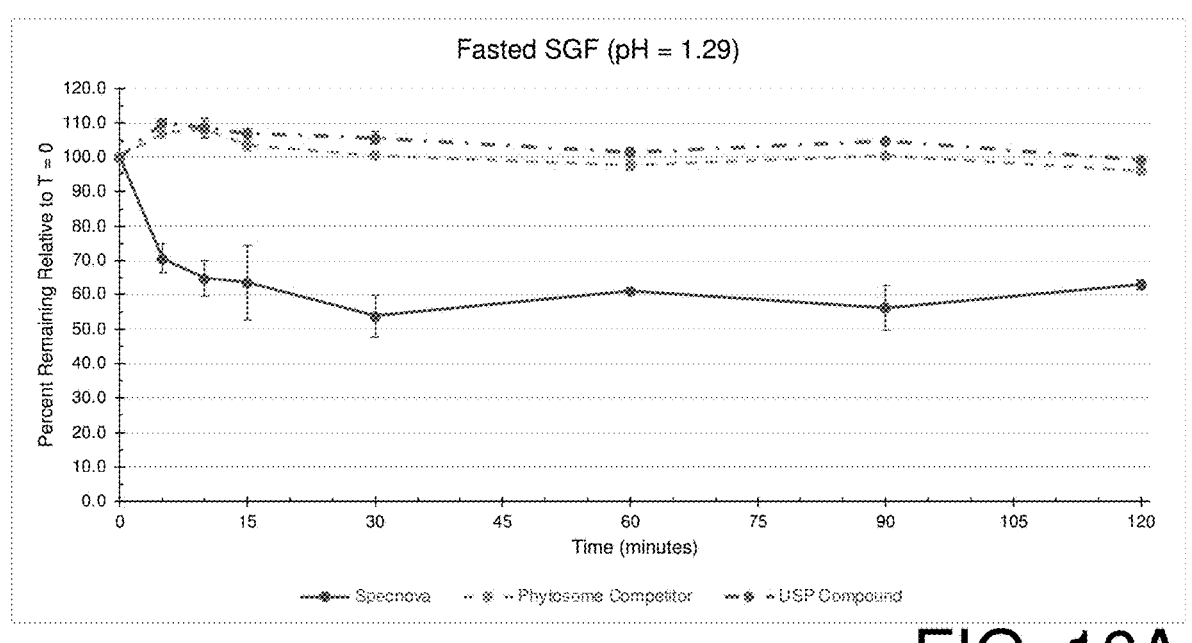
FIG. 16A is a graph of stability of quercetin products in a fasted SGF test.
FIG. 16B is a graph of stability of quercetin products in a fed SGF test.
Figure 16C:
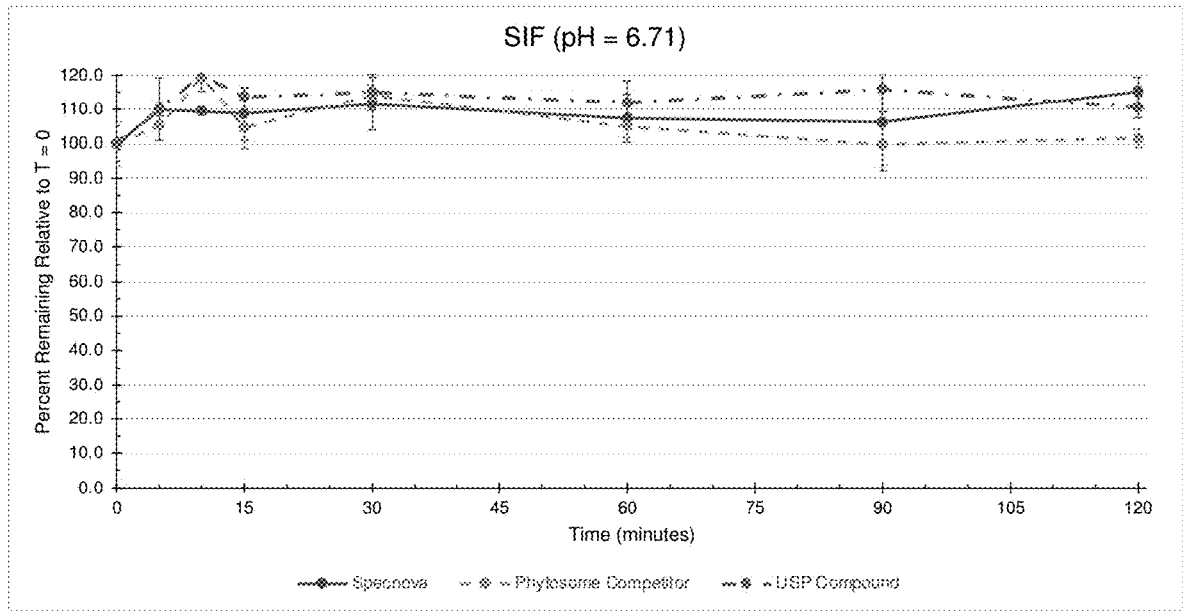
FIG. 16C is a graph of stability of quercetin products in an SIF test.

All Solutions were stable in SIF. The target product (quercetin) appears unstable at 3 μg/mL in fasted SGF. The concentration then levels off at 15 minutes through the end of the study. The competitor product and USP compound appear to be relatively stable in fasted SGF. The target product is much less stable in fed SGF, losing around 60% in two hours. The other two products are almost identical, losing around 15-20% in two hours. FIGS. 16A, 16B, 16C and Tables 24, 25, 26 summarize these results.

TABLE 24

Example 10 Stability Results - Target Product

| Time | Target Product Percent Remaining ± SD | | |
|---|---|---|---|
| (minutes) | Fasted SGF | Fed SGF | SIF |
| 0 | 100 ± 0.1 | 100 ± 6.6 | 100 ± 0.3 |
| 5 | 70.7 ± 4.2 | 87.3 ± 12.2 | 110 ± 9.1 |
| 10 | 64.9 ± 5.3 | 75.9 ± 4.5 | 109.4 ± 1 |
| 15 | 63.5 ± 10.9 | 71.7 ± 5.7 | 108.7 ± 7.6 |
| 30 | 53.8 ± 6.1 | 60.7 ± 3.9 | 111.7 ± 7.6 |
| 60 | 61 ± 0.4 | 55.6 ± 5.7 | 107.5 ± 7 |
| 90 | 56.1 ± 6.6 | 46.1 ± 1.9 | 106.3 ± 14.3 |
| 120 | 62.9 ± 1.3 | 42.9 ± 0.1 | 115.2 ± 4.3 |

TABLE 25

Example 10 Stability Results - Competitor Product

| Time | Competitor Product Percent Remaining ± SD | | |
|---|---|---|---|
| (minutes) | Fasted SGF | Fed SGF | SIF |
| 0 | 100 ± 4.4 | 100 ± 4.2 | 100 ± 6.4 |
| 5 | 107 ± 0.4 | 107.8 ± 4 | 105.3 ± 0.8 |
| 10 | 108.1 ± 2.3 | 105.6 ± 2.6 | 119.3 ± 0.2 |
| 15 | 103.6 ± 1.7 | 104 ± 1.2 | 104.6 ± 6.1 |
| 30 | 100.6 ± 0.4 | 100.7 ± 2.9 | 113.9 ± 3.4 |
| 60 | 97.7 ± 1.4 | 93.7 ± 0.2 | 105.1 ± 3.2 |
| 90 | 100.5 ± 0.8 | 91.1 ± 2.9 | 99.8 ± 5.9 |
| 120 | 96.1 ± 0.7 | 85.7 ± 0.4 | 101.5 ± 2.8 |

TABLE 26

Example 10 Stability Results - USP Compound

| Time | USP Compound Percent Remaining ± SD | | |
|---|---|---|---|
| (minutes) | Fasted SGF | Fed SGF | SIF |
| 0 | 100 ± 4.8 | 100 ± 1.5 | 100 ± 1.8 |
| 5 | 109.9 ± 1 | 104.3 ± 0.5 | 110.1 ± 1.9 |

TABLE 26-continued

Example 10 Stability Results - USP Compound

| Time | USP Compound Percent Remaining ± SD | | |
|---|---|---|---|
| (minutes) | Fasted SGF | Fed SGF | SIF |
| 10 | 108.5 ± 3 | 102.6 ± 0.3 | 120 ± 4.6 |
| 15 | 107 ± 1.2 | 100.7 ± 2.2 | 113.5 ± 0.5 |
| 30 | 105.6 ± 1.7 | 98.5 ± 1.1 | 114.9 ± 5.3 |
| 60 | 101.5 ± 1.4 | 93.4 ± 1.2 | 112.1 ± 6.3 |
| 90 | 104.8 ± 0.1 | 86.9 ± 3.4 | 115.8 ± 6.5 |
| 120 | 99.3 ± 0.4 | 79.6 ± 2.8 | 110.7 ± 3.1 |

Caco-2 Permeability Procedure

The study was performed using Caco-2 cells at a passage number of 28 seeded on a 96-well Transwell plates. Permeability was studied at a concentration of 20 μM. Compounds were solubilized in HBSS and added to apical compartment of the Transwell plate and blank buffer on basolateral side. FIG. 17 provides a visual summary of this process.

Caco-2 Permeability Results

USP pure compound had the highest permeability at 8.83±0.17*10-6 cm/sec. The target product had the least permeability at 0.3±0.04*10-6 cm/sec. The Phytosome product had the second highest permeability at 2.85±0.16*10-6 cm/sec. Table 27 summarizes these results.

TABLE 27

Example 10 Caco-2 Stability Results

| Compound | Permeability ($P_{app}$) ($*10^{-6}$ cm/sec) A-->B | Permeability Class (High/Low) |
|---|---|---|
| USP Quercetin | 8.83 ± 0.17 | High |
| Target Quercetin (Liposomal) | 0.3 ± 0.04 | Low |
| Phytosome Quercetin | 2.85 ± 0.16 | Low |
| Caffeine | 26.35 ± 3.66 | High |
| Atenolol | 3.71 ± 0.56 | Low |

Analytical Method

The parameters used in the analytical method of the example are as given below. Table 28 shows the HPLC Parameters. Table 29 shows the mass spectrometer parameters. Table 30 shows the transitions monitored. Table 31 shows the UPLC Gradient.

Linearity range: 10-2500 ng/ml

Analysis type: UPLC-MS/MS (MRM scan)

Instrument: Waters Xevo TQ-S Micro & Waters Acquity I Class UPLC

TABLE 28

Example 10 Permeability HPLC Parameters

| | |
|---|---|
| Mobile Phase A | 0.1% formic acid in water |
| Mobile Phase B | Acetonitrile |
| Flow Rate | 0.35 mL/min |
| Run Time | 3.0 minutes |
| Flow | Gradient |
| Column | Acquity UPLC BEH C18 1.7 μm, 2.1 mm × 50 mm |
| Column Temp | 40° C. |
| Sample Temp | 10° C. |
| Injection Volume | 2 μL |
| Weak Wash | 1:1:2 ACN:MeOH:water + 0.1% formic acid |
| Strong wash | 1:1:1:1 ACN:MeOH:IPA:water + 0.1% formic acid |
| Wash Volumes | Weak: 900 μL, Strong: 400 μL |

TABLE 29

Example 10 Permeability Mass Spectrometer Parameters

| | |
|---|---|
| Capillary Voltage | 2.52 kV |
| Desolvation Temp | 400° C. |
| Desolvation Gas Flow | 900 L/hr |
| Cone Gas Flow | 40 L/hr |
| Source Temp | 150° C. |

TABLE 30

Example 10 Permeability Mass Spectrometer Parameters

| | |
|---|---|
| Quercetin [M + Na]⁺ | (Quantifier) m/z 303.1 > 153.0 |
| | Cone Voltage: 50 V, Collision Voltage: 31 V |
| Quercetin [M + Na]⁺ | (Qualifier) m/z 303.1 > 137.0 |
| | Cone Voltage: 50 V, Collision Voltage: 31 V |
| Verapamil [M + Na]⁺ | (IS) m/z 455.3 > 150.1 |
| | Cone Voltage: 28 V, Collision Voltage: 42 V |

TABLE 31

Example 10 UPLC Gradient

| Time (min) | % A | Curve |
|---|---|---|
| Initial | 75 | Initial |
| 0.4 | 75 | 6 |
| 1.5 | 10 | 6 |
| 2.4 | 10 | 6 |
| 3.0 | 75 | 1 |

Calibration Curve and Representative Chromatogram

Figure 18A:
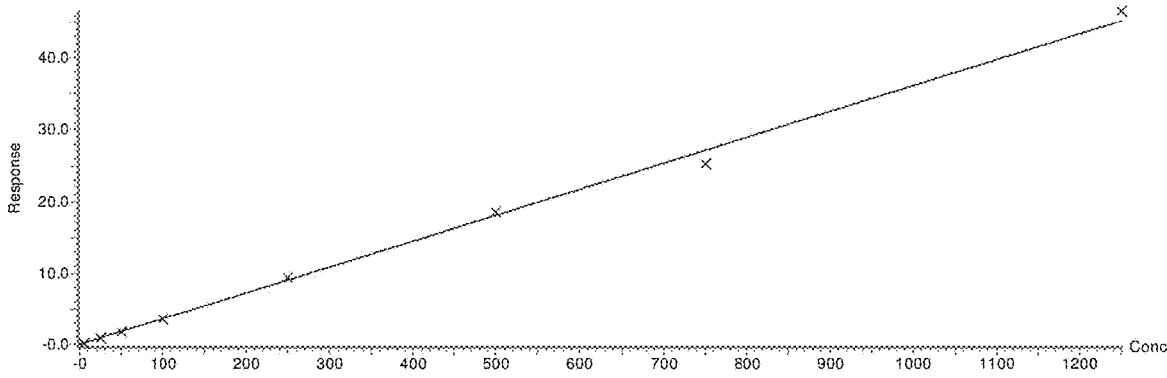
FIG. 18A is graph of a typical calibration curve for quercetin analysis.
Figure 18B:
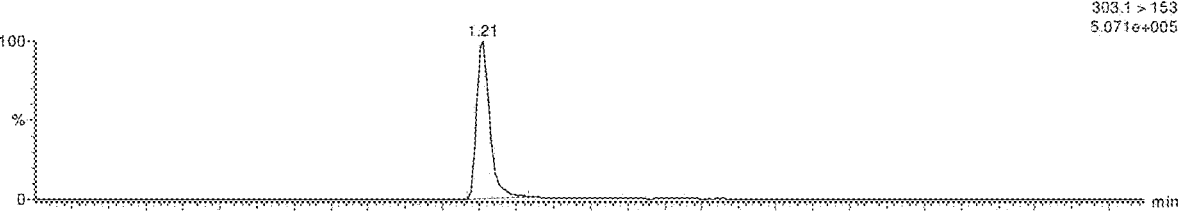
FIG. 18B is a chromatogram for quercetin.
Figure 18C:
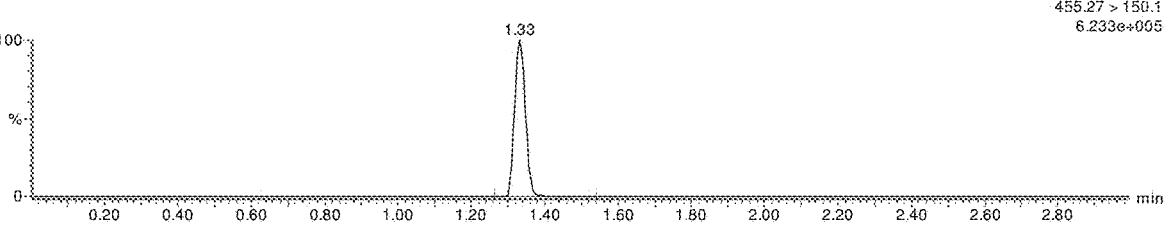
FIG. 18C is a chromatogram for verapamil, an internal standard.

FIG. 18A shows a typical calibration curve for quercetin analysis. FIG. 18B shows a chromatogram for quercetin. FIG. 18C shows a chromatogram for verapamil, the internal standard.

Example 11: Ascorbic Acid Stability in Simulated Intestinal Fluid

Quantitation Preparation

In this example, A known mass of the target product was dissolved into buffered water (pH 6.8) and diluted with 50:50 buffered water and acetonitrile (n=2). The Dr. Mercola® product was removed from its capsule and mixed with a spatula (the product was a thick oil). An amount was weighed out, suspended in methanol at a concentration of 20 mg/mL, and mixed well. Buffered water was then added for a concentration of 10 mg/mL and mixed well. The slurry was syringe-filtered, and the filtrate was diluted with 50:50 buffered water and acetonitrile (n=2).

From a working stock (WS) at 4000 ng/ml made from a USP reference standard, a standard curve from 20 to 1600 ng/ml of ascorbic acid was made with 50:50 buffered water and acetonitrile. Quality control standards were made at concentrations of 20, 60, 600, & 1200 ng/mL. Chlorothiazide at 50 ng/mL for internal standard was added to all samples, CS, and QC standards. Table 32 summarizes this information.

TABLE 32

Example 11 Quantitation Test Concentrations

| Standard | 1 | 2 | 3 | 4 | 5 | 6 | 7 | LLOQ | LQC | MQC | HQC | Unit |
|---|---|---|---|---|---|---|---|---|---|---|---|---|
| Concentration | 20 | 40 | 80 | 200 | 400 | 800 | 1600 | 20 | 60 | 600 | 1200 | ng/ml |
| WS Conc. | 4000 | 4000 | 4000 | 4000 | 4000 | 4000 | 4000 | 4000 | 4000 | 4000 | 4000 | ng/ml |
| Vol of WS | 1 | 2 | 4 | 10 | 20 | 40 | 80 | 1 | 3 | 30 | 60 | μL |
| Vol of IS | 20 | 20 | 20 | 20 | 20 | 20 | 20 | 20 | 20 | 20 | 20 | μL |
| Vol of Diluent | 179 | 178 | 176 | 170 | 160 | 140 | 100 | 179 | 177 | 150 | 120 | μL |

The total analytical volume was 200 μL for all standards and samples. Six sets of QC's were used along with the samples and seven calibration standards. All were analyzed by UPLC-MS/MS on the same day as preparation.

Quantitation Results

The target and Dr. Mercola® products contained 51.7±3.3% w/w and 64.8±0.6% w/w ascorbic acid. Table 33 summarizes these results.

TABLE 33

Example 11 Quantitation Test Results

| Sample | Percent w/w | Average | Standard Dev | Error |
|---|---|---|---|---|
| Target 1 | 48.4% | 51.7% | 0.046 | 3.3% |
| Target 2 | 54.9% | | | |
| Dr Mercola ® 1 | 64.2% | 64.8% | 0.008 | 0.6% |
| Dr Mercola ® 2 | 65.3% | | | |

Stability Experimental Conditions

Stability was performed in simulated intestinal fluid (SIF) (pH 6.8). The experimental concentration was 10 UM for both glutathione and glutathione formulation (Eq., 55%) and performed in an incubator/shaker at 37.0° C. and 125 RPM. A zero time point was taken after adding the appropriate stock to each fluid (N=2) and mixed by pipette. Time points were then taken at 5, 10, 15, 30, 60, 90, and 120 minutes. These were quenched with ACN and kept on ice until analysis. The samples were then added to 50:50 buffered water and with chlorothiazide for internal standard (IS) and filtered before analysis.

From a working stock (WS) at 4000 ng/mL made from a USP reference standard, a standard curve from 20 to 1600 ng/ml of ascorbic acid was made with 50:50 buffered water and acetonitrile. Quality control standards were made at concentrations of 20, 60, 600, & 1200 ng/mL. Chlorothiazide at 50 ng/mL for internal standard was added to all samples, CS, and QC standards. This information is summarized in Table 34.

TABLE 34

| Example 11 Stability Test Concentrations | | | | | | | | | | | | |
|---|---|---|---|---|---|---|---|---|---|---|---|---|
| Standard | 1 | 2 | 3 | 4 | 5 | 6 | 7 | LLOQ | LQC | MQC | HQC | Unit |
| Concentration | 20 | 40 | 80 | 200 | 400 | 800 | 1600 | 20 | 60 | 600 | 1200 | ng/ml |
| WS Conc. | 4000 | 4000 | 4000 | 4000 | 4000 | 4000 | 4000 | 4000 | 4000 | 4000 | 4000 | ng/ml |
| Vol of WS | 1 | 2 | 4 | 10 | 20 | 40 | 80 | 1 | 3 | 30 | 60 | μL |
| Vol of IS | 20 | 20 | 20 | 20 | 20 | 20 | 20 | 20 | 20 | 20 | 20 | μL |
| Vol of Diluent | 179 | 178 | 176 | 170 | 160 | 140 | 100 | 179 | 177 | 150 | 120 | μL |

The total analytical volume was 200 μL for all standards and samples. Six sets of QCs were used along with the samples and seven calibration standards. All were analyzed by UPLC-MS/MS on the same day as preparation.

Stability Results

Figure 19:
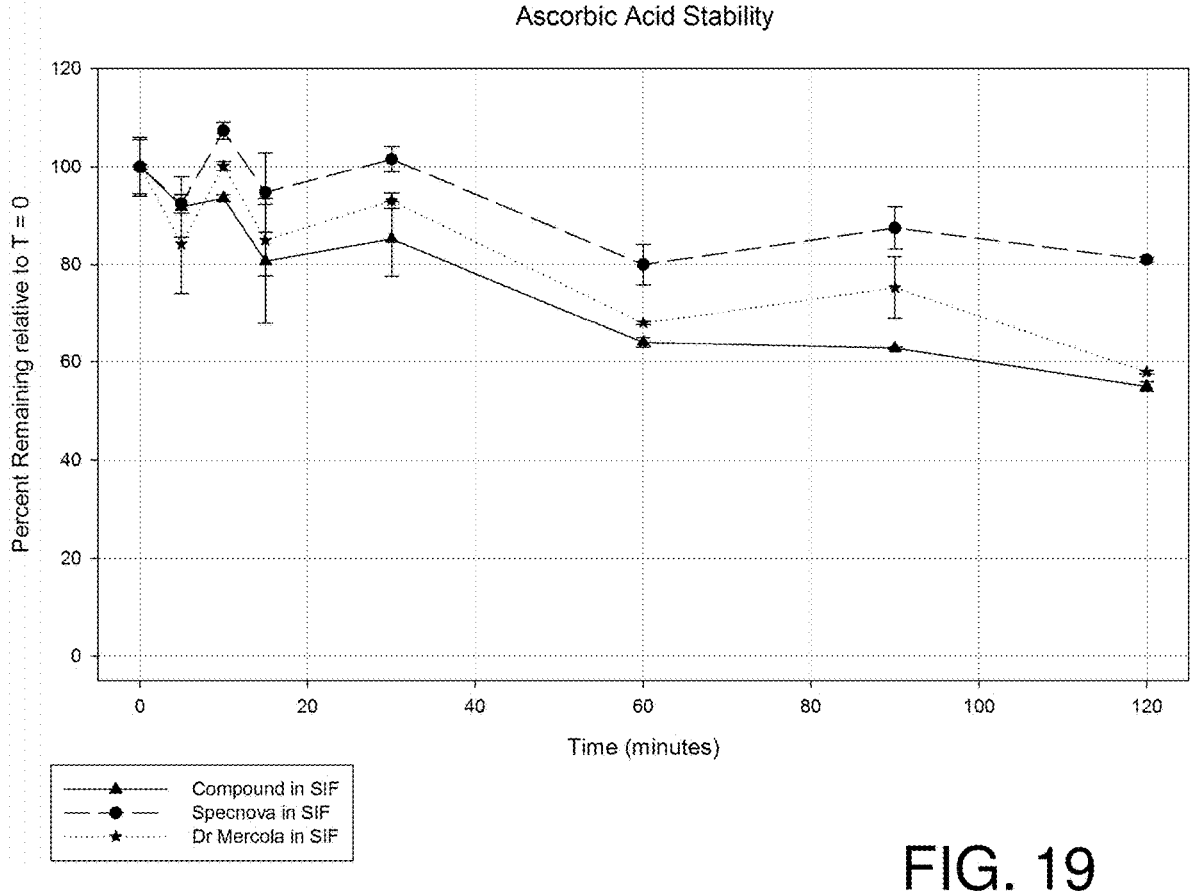
FIG. 19 is a graph of ascorbic acid stability.

The target product was the most stable in SIF (pH 6.8), losing approximately 20% over two hours. The other products were more unstable in SIF, both losing approximately 40% over two hours. FIG. 19 and Table 35 summarize these results.

TABLE 35

| | Example 11 Stability Test Results | | | | | |
|---|---|---|---|---|---|---|
| | Stability in SIF | | | | | |
| | USP compound | | Dr. Mercola ® | | Target (Liposomal) | |
| Time | % Remaining | SD | % Remaining | SD | % Remaining | SD |
| 0 | 100.0 | 6.0 | 100.0 | 5.5 | 100.0 | 0.4 |
| 5 | 91.8 | 6.1 | 84.2 | 10.1 | 92.4 | 1.8 |
| 10 | 93.6 | 0.6 | 100.2 | 0.9 | 107.4 | 1.7 |
| 15 | 80.7 | 12.7 | 85.0 | 7.3 | 94.8 | 8.1 |
| 30 | 85.3 | 7.6 | 93.0 | 1.6 | 101.6 | 2.6 |
| 60 | 64.0 | 1.0 | 68.1 | 0.4 | 80.0 | 4.1 |
| 90 | 62.8 | 0.2 | 75.4 | 6.3 | 87.5 | 4.3 |
| 120 | 55.0 | 1.0 | 57.9 | 0.4 | 81.1 | 0.5 |

N = 2 for each sample
SD = Standard deviation
SIF = Simulated Intestinal Fluid

Analytical Method

The parameters used in the analytical method of the example are as given below. Table 36 shows the HPLC Parameters. Table 37 shows the mass spectrometer parameters. Table 38 shows the UPLC Gradient.

Sample volume: 200 μL
Linearity range: 20-1600 ng/ML
Analysis type: HPLC-MS/MS

TABLE 13

| Example 9 Permeability HPLC Parameters | |
|---|---|
| Mobile Phase A | 2.5 mM ammonium acetate (pH 3.6) |
| Mobile Phase B | Acetonitrile |
| Flow Rate | 0.35 mL/min |

TABLE 13-continued

| Example 9 Permeability HPLC Parameters | |
|---|---|
| Flow | Gradient |
| Column | Acquity UPLC HSS T3 1.7 μm, 2.1 mm × 100 mm |
| Injection Volume | 2 μL |

TABLE 14

| Example 9 Permeability Mass Spectrometer Parameters | |
|---|---|
| Ascorbic Acid (Quantifier) | m/z 175.02 > 114.95 |
| Ascorbic Acid (Qualifier) | m/z 175.02 > 86.95 |
| Chlorothiazide (Int. Standard) | m/z 293.80 > 214.03 |

TABLE 15

| Example 9 UPLC Gradient | | |
|---|---|---|
| Time (min) | % A | Curve |
| Initial | 90 | Initial |
| 0.70 | 90 | 6 |
| 1.50 | 5 | 6 |
| 2.00 | 5 | 6 |
| 2.50 | 90 | 1 |

Calibration Curve and Representative Chromatogram

Figure 20A:
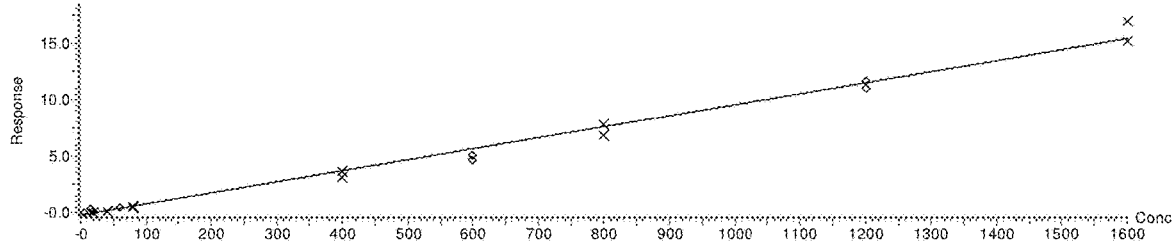
FIG. 20A is graph of a typical calibration curve for ascorbic acid analysis.
Figure 20B:
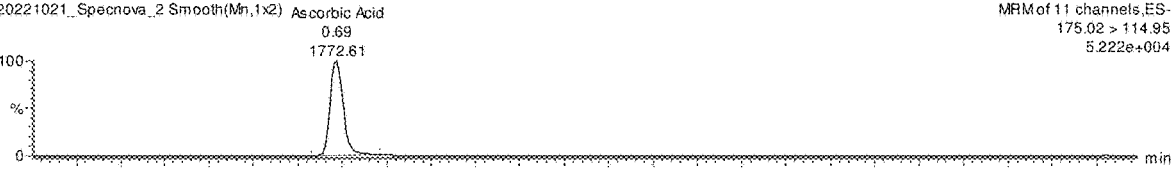
FIG. 20B is a chromatogram for ascorbic acid.
Figure 20C:
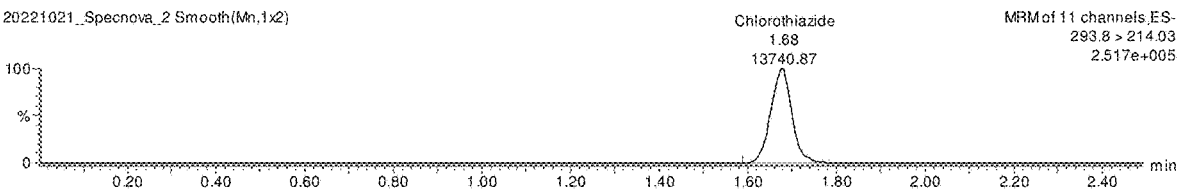
FIG. 20C is a chromatogram for chlorothiazide, an internal standard.

FIG. 20A shows a typical calibration curve for ascorbic acid analysis. FIG. 20B shows a chromatogram for ascorbic acid. FIG. 20C shows a chromatogram for chlorothiazide, the internal standard.

Although the disclosure has been described with reference to preferred embodiments, persons skilled in the art will recognize that changes may be made in form and detail without departing from the spirit and scope of the disclosed apparatus, systems and methods.

What is claimed is:

1. A liposomal composition for sustained release of an active comprising:

a) a first liposomal core comprising Phosphatidylcholine (PC), phosphatidylethanolamine (PE), phosphatidylserine (PS) and the active dispersed within the first liposomal core; and b) a second core surrounding the first liposomal core, the second core comprising one or more polypeptide and at least one polysaccharide.

2. The liposomal composition of claim 1, wherein the amount of PC in the first liposomal core is at least about 50 wt %.

3. The liposomal composition of claim 2, wherein the amount of PE in the first liposomal core is from about 5-8 wt %.

4. The liposomal composition of claim 3, wherein the amount of PS in the first liposomal core is from about 8-10 wt %.

5. The liposomal composition of claim 1, wherein the first liposomal core has a phase transition temperature of at least about 37° C.

6. The liposomal composition of claim 1, wherein the second core polypeptide comprises pea protein hydrolysate and/or brown rice protein.

7. The liposomal composition of claim 6, wherein the second core polypeptide comprises at least about 10 wt % dipeptides and tripeptides.

8. The liposomal composition of claim 1, wherein the second core polysaccharide comprises sodium hyaluronate, gum Arabic, sodium alginate and/or trehalose.

9. The liposomal composition of claim 8, wherein the second core polysaccharide has a positive charge.

10. The liposomal composition of claim 8, wherein the second core polysaccharide has a negative charge.

11. The liposomal composition of claim 1, wherein the liposomal composition further comprises a coating of ethyl cellulose.

12. The liposomal composition of claim 11, wherein the liposomal composition exhibits an increased in sustained release of the active relative to an otherwise identical liposomal composition without a coating of ethyl cellulose.

13. The liposomal composition of claim 1, where in the second liposomal core has a diameter of about 200 nm or less.

14. The liposomal composition of claim 13, where in the second liposomal core has a diameter of from about 140-185 nm.

15. The liposomal composition of claim 14, where in the second liposomal core has a diameter of about 145 nm.

16. The liposomal composition of claim 1, wherein the first and second liposomal cores of the liposomal composition collectively have a zeta potential of from about −30.1 meV to about −61.8 meV.

17. The liposomal composition of claim 1, wherein the liposomal composition releases a greater percentage of the active in simulated intestinal fluid (SIF) than in simulated gastric fluid (SGF).

18. The liposomal composition of claim 1, wherein the composition has an entrapment efficacy of at least about 80 wt %.

19. The liposomal composition of claim 1, wherein the liposomal composition remains stable for at least about 240 days when stored at a temperature of from about 20° C. to about 25° C.

* * * * *